(12) United States Patent
Nielsen et al.

(10) Patent No.: US 11,613,768 B2
(45) Date of Patent: Mar. 28, 2023

(54) MICROBIAL PRODUCTION OF 2-PHENYLETHANOL FROM RENEWABLE SUBSTRATES

(71) Applicant: Arizona Board of Regents on behalf of Arizona State University, Scottsdale, AZ (US)

(72) Inventors: David Nielsen, Tempe, AZ (US); Michael Machas, Phoenix, AZ (US); Rebekah McKenna, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 313 days.

(21) Appl. No.: 16/633,525

(22) PCT Filed: Jul. 18, 2018

(86) PCT No.: PCT/US2018/042687
§ 371 (c)(1),
(2) Date: Jan. 23, 2020

(87) PCT Pub. No.: WO2019/023019
PCT Pub. Date: Jan. 31, 2019

(65) Prior Publication Data
US 2020/0231992 A1    Jul. 23, 2020

Related U.S. Application Data

(60) Provisional application No. 62/536,666, filed on Jul. 25, 2017.

(51) Int. Cl.
*C12N 1/20*    (2006.01)
*C12P 7/22*    (2006.01)
(Continued)

(52) U.S. Cl.
CPC ............... *C12P 7/22* (2013.01); *C12N 1/20* (2013.01); *C12N 9/88* (2013.01); *C12N 1/205* (2021.05);
(Continued)

(58) Field of Classification Search
None
See application file for complete search history.

(56) References Cited

U.S. PATENT DOCUMENTS 3,660,235 A    5/1972    Okumura
4,681,852 A    7/1987    Tribe
(Continued)

FOREIGN PATENT DOCUMENTS

EP    0321488    6/1989
JP    H05153978    6/1993
(Continued)

OTHER PUBLICATIONS

Singapore Application No. 102017041820, filed May 23, 2017 (Year: 2017).*

(Continued)

*Primary Examiner* — Richard C Ekstrom
(74) *Attorney, Agent, or Firm* — Quarles & Brady LLP

(57) ABSTRACT

Described herein are engineered metabolic pathways in recombinant microorganism host cells which result in the production of 2-phenylethanol or 2-phenylacetic acid. Also described herein are methods of using the recombinant microorganisms for the production of 2-phenylethanol or 2-phenylacetic acid.

14 Claims, 10 Drawing Sheets

Specification includes a Sequence Listing.

(51) Int. Cl.
*C12N 9/88* (2006.01)
*C12R 1/19* (2006.01)

(52) U.S. Cl.
CPC ... *C12R 2001/19* (2021.05); *C12Y 102/01039* (2013.01); *C12Y 114/14011* (2013.01); *C12Y 403/01024* (2013.01); *C12Y 503/99007* (2013.01)

(56) References Cited

U.S. PATENT DOCUMENTS

| | | | |
|---|---|---|---|
| 9,150,884 | B2 | 10/2015 | Nielsen |
| 9,944,955 | B1 | 4/2018 | Wang et al. |
| 10,125,377 | B2 | 11/2018 | Nielsen et al. |
| 10,174,346 | B2 | 1/2019 | Nielsen et al. |
| 10,246,726 | B2 | 4/2019 | Wang |
| 2011/0256595 | A1 | 10/2011 | Yoshinkuni |
| 2014/0057325 | A1 | 2/2014 | Nielsen |
| 2017/0067084 | A1 | 3/2017 | Li et al. |
| 2019/0194695 | A1 | 6/2019 | Nielsen et al. |
| 2020/0216865 | A1 | 7/2020 | Nielsen et al. |
| 2020/0231992 | A1* | 7/2020 | Nielsen ............... C12N 9/0008 |
| 2020/0232000 | A1* | 7/2020 | Li ............................ C12N 9/88 |

FOREIGN PATENT DOCUMENTS

| | | |
|---|---|---|
| WO | 1993007270 | 4/1993 |
| WO | 1997032023 | 9/1997 |
| WO | 1998011205 | 3/1998 |
| WO | 2012122333 A1 | 9/2012 |
| WO | 2013172928 A1 | 11/2013 |
| WO | 2015031048 A1 | 3/2015 |
| WO | 2015041776 A1 | 3/2015 |
| WO | 2019018302 A1 | 1/2019 |

OTHER PUBLICATIONS

Gen Bank Accession No. ABB03729.1, published Sep. 1, 2006 (Year: 2006).*
Achmon, Y., et al., 2011. Hydrophobic microspheres for in situ removal of 2-phenylethanol from yeast fermentation. Journal of Microencapsulation. 28, 628-638.
Atsumi, S., et al. Non-fermentative pathways for synthesis of branched-chain higher alcohols as biofuels. Nature 451, 86-9 (2008).
Baez-Viveros, J. L., et al. "Metabolic engineering and protein directed evolution increase the yield of L-phenylalanine synthesized from glucose in *Escherichia coli*." Biotechnology and bioengineering 87.4 (2004): 516-524.
Datsenko, K. A. et al. One-step inactivation of chromosomal genes in *Escherichia coli* K-12 using PCR products. Proc. Natl. Acad. Sci. U. S. A. 97, 6640-5 (2000).
De Mey, M., et al. Minimizing acetate formation in *E. coli* fermentations. J. Ind. Microbiol. Biotechnol. 34, 689-700 (2007).
Dickinson, J. R., et al. The catabolism of amino acids to long chain and complex alcohols in *Saccharomyces cerevisiae*. J. Biol. Chem. 278, 8028-34 (2003).
Etschmann, M. M. W., et al. Biotechnological production of 2-phenylethanol. Appl. Microbiol. Biotechnol. 59, 1-8 (2002).
Etschmann, M. M. W., et al. Screening of yeasts for the production of the aroma compound 2-phenylethanol in a molasses-based medium. Biotechnol. Lett. 25, 531-536. 2003.
Etschmann, M. M. W., et al., 2005. Production of 2-phenylethanol and 2-phenylethylacetate from L-phenylalanine by coupling whole-cell biocatalysis with organophilic pervaporation. Biotechnology and Bioengineering. 92, 624-634.
Flamholz, A., et al. eQuilibrator—the biochemical thermodynamics calculator. Nucleic Acids Res. 40, D770-5 (2012).
Gelfand, D. H., et al., 1977. *Escherichia coli* mutants deficient in the aspartate and aromatic amino acid aminotransferases. Journal of Bacteriology. 130, 429-440.

Gosset, G. et al. Improvement of *Escherichia coli* production strains by modification of the phosphoenolpyruvate: sugar phosphotransferase system. Microb. Cell Fact. 4, 14 (2005).
Hayashi, H., et al. *Escherichia coli* aromatic amino acid aminotransferase: characterization and comparison with aspartate aminotransferase. Biochemistry 32, 12229-39 (1993).
Hazelwood, L. A., et al., 2008. The Ehrlich pathway for fusel alcohol production: a century of research on *Saccharomyces cerevisiae* metabolism. Appl Environ Microbiol. 74, 2259-66.
Ho, K. K., et al., 2005. Isolation and Characterization of an Aldehyde Dehydrogenase Encoded by the aldB Gene of *Escherichia coli*. Journal of Bacteriology. 187, 1067-1073.
Hsieh, L.-S. et al. Cloning and expression of a phenylalanine ammonia-lyase gene (BoPAL2) from Bambusa oldhamii in *Escherichia coli* and Pichia pastoris. Protein Expr. Purif. 71, 224-30 (2010).
Hua, D. et al. Recent advances in biotechnological production of 2-phenylethanol. Biotechnol. Adv. 29, 654-60 (2011).
International Searching Authority, International Search Report and Written Opinion for application PCT/US2018/042687, dated Nov. 9, 2018.
Iraqui, I., et al. Characterisation of *Saccharomyces cerevisiae* ARO8 and ARO9 genes encoding aromatic aminotransferases I and II reveals a new aminotransferase subfamily. Mol. Gen. Genet. 257, 238-48 (1998).
Juminaga, D. et al. Modular engineering of L-tyrosine production in *Escherichia coli*. Appl. Environ. Microbiol. 78, 89-98 (2012).
Kang, Z., et al. Metabolic engineering of *Escherichia coli* for production of 2-phenylethanol from renewable glucose. Appl. Biochem. Biotechnol. 172, 2012-21 (2014).
Kieser, M. E., et al. Determination of 2-Phenylethanol in Cider. Nature 204, 887-887 (1964).
Kim, B., et al. Metabolic engineering of *Saccharomyces cerevisiae* for the production of 2-phenylethanol via Ehrlich pathway. Biotechnol. Bioeng. 111, 115-124 (2014).
Kim, T.-Y., et al. Biosynthesis of 2-phenylethanol from glucose with genetically engineered Kluyveromyces marxianus. Enzyme Microb. Technol. 61, 44-47 (2014).
Kneen, M. M., et al. 2011. Characterization of a thiamin diphosphate-dependent phenylpyruvate decarboxylase from *Saccharomyces cerevisiae*. FEBS Journal. 278, 1842-1853.
Koma, D., et al. Production of aromatic compounds by metabolically engineered *Escherichia coli* with an expanded shikimate pathway. Appl. Environ. Microbiol. 78, 6203-6216 (2012).
Kunjapur, A. M., et al. Synthesis and Accumulation of Aromatic Aldehydes in an Engineered Strain of *Escherichia coli*. J. Am. Chem. Soc. 136, 11644-11654 (2014).
Lee, C.-W. et al. Catabolism of L-phenylalanine by some microorganisms of cheese origin. J. Dairy Res. 51, 461 (1984).
Liu, S. P., et al., 2014. A systems level engineered *E. coli* capable of efficiently producing L-phenylalanine. Process Biochemistry. 49, 751-757.
McKenna, R. et al. Styrene biosynthesis from glucose by engineered *E. coli*. Metab. Eng. 13, 544-54 (2011).
McKenna, R., et al. Microbial production of the aromatic building-blocks (S)-styrene oxide and (R)-1,2-phenylethanediol from renewable resources. Biotechnol. J. 8, 1465-75 (2013).
Noda, S., et al. Metabolic design of a platform *Escherichia coli* strain producing various chorismate derivatives. Metab. Eng. 33, 119-29 (2016).
O'Connor, K., et al. Possible regulatory role for nonaromatic carbon sources in styrene degradation by Pseudomonas putida CA-3. Appl. Environ. Microbiol. 61, 544-8 (1995).
O'leary, N. D., et al. "Biochemistry, genetics and physiology of microbial styrene degradation." FEMS microbiology reviews 26.4 (2002): 403-417.
Panke, S., et al. Towards a biocatalyst for (S)-styrene oxide production: characterization of the styrene degradation pathway of *Pseudomonas* sp. strain VLB120. Appl. Environ. Microbiol. 64, 2032-43 (1998).
Parrott, S., et al. 2-Phenylethylamine catabolism by *Escherichia coli* K12. J. Gen. Microbiol. 133, 347-51 (1987).

(56) References Cited

OTHER PUBLICATIONS

Powell, J. T. et al. The Purification and Properties of the Aspartate Aminotransferase and Aromatic-Amino-Acid Aminotransferase from *Escherichia coli*. Eur. J. Biochem. 87, 391-400 (1978).

Pugh, S., et al. Engineering *Escherichia coli* for renewable benzyl alcohol production. Metab. Eng. Commun. 2, 39-45 (2015).

Pugh, S., et al. Rational engineering of a novel pathway for producing the aromatic compounds p-hydroxybenzoate, protocatechuate, and catechol in *Escherichia coli*. Process Biochem. 49, 1843-1850 (2014).

Reichert, A. I., et al. Phenylalanine ammonia-lyase (PAL) from tobacco (*Nicotiana tabacum*): characterization of the four tobacco PAL genes and active heterotetrameric enzymes. Biochem. J. 424, 233-42 (2009).

Rodriguez, G. M. et al. Toward aldehyde and alkane production by removing aldehyde reductase activity in *Escherichia coli*. Metab. Eng. 25, 227-37 (2014).

Sendovski, M., et al., 2010. Bioproduction of 2-Phenylethanol in a Biphasic Ionic Liquid Aqueous System. Journal of Agricultural and Food Chemistry. 58, 2260-2265.

Shankar, V. S. B., et al., 2017. Antiknock quality and ignition kinetics of 2-phenylethanol, a novel lignocellulosic octane booster. Proceedings of the Combustion Institute. 36, 3515-3522.

Shen, L., et al. Overexpressing enzymes of the Ehrlich pathway and deleting genes of the competing pathway in *Saccharomyces cerevisiae* for increasing 2-phenylethanol production from glucose. J. Biosci. Bioeng. 122, 34-39 (2016).

Sikkema, J., et al. Interactions of cyclic hydrocarbons with biological membranes. J. Biol. Chem. 269, 8022-8 (1994).

Suastegui, M. et al. Yeast factories for the production of aromatic compounds: from building blocks to plant secondary metabolites. J. Ind. Microbiol. Biotechnol. 43, 1611-1624 (2016).

Tan, Z., et al., 2016. Membrane engineering via trans unsaturated fatty acids production improves *Escherichia coli* robustness and production of biorenewables. Metabolic Engineering. 35, 105-113.

Thompson, B., et al. Engineering and comparison of non-natural pathways for microbial phenol production. Biotechnol. Bioeng. 113, 1745-1754 (2016).

Tian, M., et al., 2015. Lignin Derivatives as Potential Octane Boosters. SAE Int. J. Fuels Lubr. 8, 415-422.

Tieman, D et al. Tomato aromatic amino acid decarboxylases participate in synthesis of the flavor volatiles 2-phenylethanol and 2-phenylacetaldehyde. Proc. Natl. Acad. Sci. U. S. A. 103, 8287-92 (2006).

U.S. Appl. No. 16/894,416, filed Jun. 5, 2020, Nielsen et al.

Varma, A., et al., 1993. Biochemical production capabilities of *Escherichia coli*. Biotechnology and Bioengineering. 42, 59-73.

Vuralhan, Z. et al. Physiological characterization of the ARO10-dependent, broad-substrate-specificity 2-oxo acid decarboxylase activity of *Saccharomyces cerevisiae*. Appl. Environ Microbiol 71, 3276-84 (2005).

Wang, Z., et al. "Regulation of crucial enzymes and transcription factors on 2-phenylethanol biosynthesis via Ehrlich pathway in *Saccharomyces cerevisiae*." Journal of industrial microbiology & biotechnology 44.1 (2017): 129-139.

Warhurst, A. M. et al. Microbial metabolism and biotransformations of styrene. J. Appl. Bacteriol. 77, 597-606 (1994).

Xu, B., et al., 1999. Glucose overflow metabolism and mixed-acid fermentation in aerobic large-scale fed-batch processes with *Escherichia coli*. Appl Microbiol Biotechnol. 51, 564-571.

\* cited by examiner

SEQUENCE LISTING

<160> NUMBER OF SEQ ID NOS: 15

<210> SEQ ID NO 1
<211> LENGTH: 2154
<212> TYPE: DNA
<213> ORGANISM: Arabidopsis thaliana

<400> SEQUENCE: 1

| | | | | | | |
|---|---|---|---|---|---|---|
| atggatcaaa | tcgaagcaat | gttgtgcggc | ggaggagaga | agacaaaagt | ggcggttact | 60 |
| acgaagactt | tggcagatcc | attgaattgg | ggtttagcag | cggatcaaat | gaaaggaagt | 120 |
| catttagatg | aagtgaagaa | gatggtcgaa | gagtatcgta | gaccagtcgt | gaatcttggc | 180 |
| ggagaaacac | tgacgatcgg | acaagttgct | gccatctcca | ccgtaggagg | cagcgttaag | 240 |
| gttgagttag | cggagacttc | aagagccggt | gtgaaagcta | gcagtgattg | ggttatggag | 300 |
| agcatgaaca | aagtactga | cagttacgga | gtcaccaccg | gctttggtgc | tacttctcac | 360 |
| cggagaacca | aaaacggcac | cgcattacaa | acagaactca | ttagatttt | gaacgccgga | 420 |
| atattcggaa | acacgaagga | gacatgtcac | acactgccgc | aatccgccac | aagagccgcc | 480 |
| atgctcgtca | gagtcaacac | tcttctccaa | ggatactccg | ggatccgatt | cgagatcctc | 540 |
| gaagcgatta | caagtctcct | caaccacaac | atctctccgt | cactacctct | ccgtggaacc | 600 |
| attaccgcct | ccggcgatct | cgttcctctc | tcttacatcg | ccggacttct | caccggccgt | 660 |
| cctaattcca | aagccaccgg | tcccgacggt | gaatcgctaa | ccgcgaaaga | agcttttgag | 720 |
| aaagccggaa | tcagtactgg | attcttcgat | ttacaaccta | aggaaggttt | agctctcgtt | 780 |
| aatggcacgg | cggttggatc | tggaatggcg | tcgatggttc | tattcgaagc | gaatgtccaa | 840 |
| gcggtgttag | cggaggtttt | atcagcgatc | ttcgcggagg | ttatgagcgg | gaaacctgag | 900 |
| tttaccgatc | atctgactca | tcgtttaaaa | catcatcccg | gacaaatcga | agcggcggcg | 960 |
| ataatggagc | acatactcga | cggaagctca | tacatgaaat | tagctcaaaa | ggttcacgag | 1020 |
| atggatccat | tgcagaaacc | aaaacaagat | cgttacgctc | ttcgtacatc | tcctcaatgg | 1080 |
| ctaggtcctc | aaattgaagt | aatccgtcaa | gctacgaaat | cgatagagcg | tgaaatcaac | 1140 |
| tccgttaacg | ataatccgtt | gatcgatgtt | tcgaggaaca | aggcgattca | cggtggtaac | 1200 |
| ttccaaggaa | caccaatcgg | agtttctatg | gataacacga | gattggcgat | tgctgcgatt | 1260 |
| gggaagctaa | tgtttgctca | attctctgag | cttgttaatg | atttctacaa | caatggactt | 1320 |
| ccttcgaatc | taactgcttc | gagtaatcca | agtttggatt | atggattcaa | aggagcagag | 1380 |
| attgctatgg | cttcttattg | ttctgagctt | caatacttgg | ctaatccagt | cacaagccat | 1440 |
| gttcaatcag | ctgagcaaca | taatcaagat | gtgaactctc | ttggtttgat | ctcgtctcgt | 1500 |
| aaaacatctg | aagctgtgga | tattcttaag | ctaatgtcaa | caacgttcct | tgtggggata | 1560 |
| tgtcaagctg | ttgatttgag | acatttggag | gagaatctga | gacaaactgt | gaagaacaca | 1620 |
| gtttctcaag | ttgctaagaa | agtgttaacc | actggaatca | acggtgagtt | acatccgtca | 1680 |
| aggttttgcg | agaaggactt | gcttaaggtt | gttgatcgtg | agcaagtgtt | cacgtatgtg | 1740 |
| gatgatcctt | gtagcgctac | gtaccgttg | atgcagagac | taagacaagt | tattgttgat | 1800 |
| cacgctttgt | ccaacggtga | gactgagaag | aatgcagtga | cttcgatctt | tcaaaagatt | 1860 |
| ggagcttttg | aagaggagct | taaggctgtg | cttccaaagg | aagttgaagc | ggctagagcg | 1920 |
| gcttatggga | atggaactgc | gccgattcct | aaccggatta | ggaatgtag | gtcgtatccg | 1980 |
| ttgtataggt | tcgtgaggga | agagcttgga | acgaagttgt | tgactggaga | aaaggttgtg | 2040 |
| tctccgggag | aggagtttga | taaggtcttc | actgctatgt | gtgaaggtaa | acttattgat | 2100 |

```
ccgttgatgg attgtctcaa ggaatggaac ggagctccga ttccgatttg ctaa      2154
```

<210> SEQ ID NO 2
<211> LENGTH: 1512
<212> TYPE: DNA
<213> ORGANISM: Saccharomyces cerevisiae

<400> SEQUENCE: 2

```
atgaggaagc taaatccagc tttagaattt agagacttta tccaggtctt aaaagatgaa    60
gatgacttaa tcgaaattac cgaagagatt gatccaaatc tcgaagtagg tgcaattatg   120
aggaaggcct atgaatccca cttaccagcc ccgttattta aaaatctcaa aggtgcttcg   180
aaggatcttt tcagcatttt aggttgccca gccggtttga agtaagga gaaaggagat    240
catggtagaa ttgcccatca tctgggggctc gacccaaaaa caactatcaa ggaaatcata   300
gattatttgc tggagtgtaa ggagaaggaa cctctccccc caatcactgt tcctgtgtca   360
tctgcacctt gtaaaacaca tatactttct gaagaaaaaa tacatctaca agcctgcca    420
acaccatatc tacatgtttc agacggtggc aagtacttac aaacgtacgg aatgtggatt   480
cttcaaactc cagataaaaa atggactaat tggtcaattg ctagaggtat ggttgtagat   540
gacaagcata tcactggtct ggtaattaaa ccacaacata ttagacaaat tgctgactct   600
tgggcagcaa ttggaaaagc aaatgaaatt ccttcgcgt tatgttttgg cgttcccca    660
gcagctattt tagttagttc catgccaatt cctgaaggtg tttctgaatc ggattatgtt   720
ggcgcaatct gggtgagtc ggttccagta gtaaaatgtg agaccaacga tttaatggtt   780
cctgcaacga gtgagatggt atttgagggt actttgtcct aacagatac acatctggaa   840
ggcccatttg gtgagatgca tggatatgtt ttcaaaagcc aaggtcatcc ttgtccattg   900
tacactgtca aggctatgag ttacagagac aatgctattc tacctgtttc gaaccccggt   960
ctttgtacgg atgagacaca taccttgatt ggttcactag tggctactga ggccaaggag  1020
ctggctattg aatctggctt gccaattctg gatgcctta tgccttatga ggctcaggct  1080
ctttggctta tcttaaaggt ggatttgaaa gggctgcaag cattgaagac aacgcctgaa  1140
gaattttgta agaaggtagg tgatatttac tttaggacaa aagttggttt tatagtccat  1200
gaataatttt ggtggcaga tgatatcgac atatttaact tcaaagaagt catctgggcc  1260
tacgttacaa gacatacacc tgttgcagat cagatggctt ttgatgatgt cacttctttt  1320
cctttggctc cctttgtttc gcagtcatcc agaagtaaga ctatgaaagg tggaaagtgc  1380
gttactaatt gcatatttag acagcaatat gagcgcagtt ttgactacat aacttgtaat  1440
tttgaaaagg gatatccaaa aggattagtt gacaaagtaa atgaaaattg gaaaaggtac  1500
ggatataaat aa                                                       1512
```

<210> SEQ ID NO 3
<211> LENGTH: 1248
<212> TYPE: DNA
<213> ORGANISM: Pseudomonas putida

<400> SEQUENCE: 3

```
atgaaaaagc gtatcggtat tgttggtgca ggcactgccg gcctccatct tggtctcttc    60
cttcgtcagc atgacgtcga cgtcactgtg tacactgatc gtaagcccga tgagtacagc   120
ggactgcgtc tcctgaatac cgttgctcac aacgcggtga cggtgcagcg ggaggttgcc   180
ctcgacgtca atgagtggcc gtctgaggag tttggttatt tcggccacta ctactacgta   240
```

-continued

| | |
|---|---|
| ggtgggccgc agcccatgcg tttctacggt gatctcaagg ctcccagccg tgcagtggac | 300 |
| taccgtctct accagccgat gctgatgcgt gcactggaag ccaggggcgg caagttctgc | 360 |
| tacgacgcgg tgtctgccga agatctggaa gggctgtcgg agcagtacga tctgctggtt | 420 |
| gtgtgcactg gtaaatacgc cctcggcaag gtgttcgaga agcagtccga aaactcgccc | 480 |
| ttcgagaagc cgcaacgggc actgtgcgtt ggtctcttca agggcatcaa ggaagcaccg | 540 |
| attcgcgcgg tgactatgtc cttctcgcca gggcatggcg agctgattga gattccaacc | 600 |
| ctgtcgttca atggcatgag cacagcgctg gtgctcgaaa accatattgg tagcgatctg | 660 |
| gaagttctcg cccacaccaa gtatgacgat gacccgcgtg cgttcctcga tctgatgctg | 720 |
| gagaagctgg gtaagcatca tccttccgtt gccgagcgca tcgatccggc tgagttcgac | 780 |
| cttgccaaca gttctctgga catcctccag ggtggtgttg tgccggcatt ccgcgacggt | 840 |
| catgcgaccc tcaataacgg caaaaccatc attgggctgg gcgacatcca ggcaactgtc | 900 |
| gatccggtct ggggccaggg cgcgaacatg gcgtcctatg cggcatggat tctgggcgag | 960 |
| gaaatccttg cgcactctgt ctacgacctg cgcttcagcg aacacctgga gcgtcgccgc | 1020 |
| caggatcgcg tgctgtgtgc cacgcgatgg accaacttca ctctgagcgc tctctcggca | 1080 |
| cttccgccgg agttcctcgc cttccttcag atcctgagcc agagccgtga atggctgat | 1140 |
| gagttcacgg acaacttcaa ctaccccgga cgtcagtggg atcgcttctc cagcccggaa | 1200 |
| cgtatcggac agtggtgcag tcagttcgca cccactatcg cggcctga | 1248 |

<210> SEQ ID NO 4
<211> LENGTH: 513
<212> TYPE: DNA
<213> ORGANISM: Pseudomonas putida

<400> SEQUENCE: 4

| | |
|---|---|
| atgacgttaa aaaagatat ggcggtggat atcgactcca ccaacttccg ccaggcggtt | 60 |
| gcattgttcg cgacgggaat tgcggttctc agcgcggaga ctgaagaggg cgatgtgcac | 120 |
| ggcatgaccg tgaacagttt cacctccatc agtctggatc cgccgactgt gatggtttcc | 180 |
| ctgaaatcgg gccgtatgca tgagttgctg actcaaggcg gacgcttcgg agttagcctc | 240 |
| ttgggtgaaa gccagaaggt gttctcggca ttcttcagca gcgcgcgat ggatgacacg | 300 |
| cctccccccg ccttcaccat tcaggccggc cttcccactc tgcagggcgc catggcctgg | 360 |
| ttcgaatgcg aggtggagag cacggttcaa gtacacgacc acacgctctt cattgcgcgc | 420 |
| gttagcgcct gtggaacgcc tgaggcgaat accccccagc cgctgctgtt ctttgccagc | 480 |
| cgttatcacg gcaacccgtt gccactgaat tga | 513 |

<210> SEQ ID NO 5
<211> LENGTH: 1815
<212> TYPE: DNA
<213> ORGANISM: Pseudomonas putida

<400> SEQUENCE: 5

| | |
|---|---|
| atgaaaaagc gtatcggtat tgttggtgca ggcactgccg gcctccatct ggtctcttc | 60 |
| cttcgtcagc atgacgtcga cgtcactgtg tacactgatc gtaagcccga tgagtacagc | 120 |
| ggactgcgtc tcctgaatac cgttgctcac aacgcggtga cggtgcagcg ggaggttgcc | 180 |
| ctcgacgtca atgagtggcc gtctgaggag tttggttatt cggccactac tactacgta | 240 |
| ggtgggccgc agcccatgcg tttctacggt gatctcaagg ctcccagccg tgcagtggac | 300 |
| taccgtctct accagccgat gctgatgcgt gcactggaag ccaggggcgg caagttctgc | 360 |

```
tacgacgcgg tgtctgccga agatctggaa gggctgtcgg agcagtacga tctgctggtt    420
gtgtgcactg gtaaatacgc cctcggcaag gtgttcgaga agcagtccga aaactcgccc    480
ttcgagaagc cgcaacgggc actgtgcgtt ggtctcttca agggcatcaa ggaagcaccg    540
attcgcgcgt tgactatgtc cttctcgcca gggcatggcg agctgattga gattccaacc    600
ctgtcgttca atggcatgag cacagcgctg gtgctcgaaa accatattgg tagcgatctg    660
gaagttctcg cccacaccaa gtatgacgat gacccgcgtg cgttcctcga tctgatgctg    720
gagaagctgg gtaagcatca tccttccgtt gccgagcgca tcgatccggc tgagttcgac    780
cttgccaaca gttctctgga catcctccag ggtggtgttg tgccggcatt ccgcgacggt    840
catgcgaccc tcaataacgg caaaaccatc attgggctgg gcgacatcca ggcaactgtc    900
gatccggtct gggccagggg cgcgaacatg gcgtcctatg cggcatggat tctgggcgag    960
gaaatccttg cgcactctgt ctacgacctg cgcttcagcg aacacctgga gcgtcgccgc   1020
caggatcgcg tgctgtgtgc cacgcgatgg accaacttca ctctgagcgc tctctcggca   1080
cttccgccgg agttcctcgc cttccttcag atcctgagcc agagccgtga aatggctgat   1140
gagttcacgg acaacttcaa ctacccggaa cgtcagtggg atcgcttctc cagcccggaa   1200
cgtatcggac agtggtgcag tcagttcgca cccactatcg cggcctgacg ctattgctcc   1260
gctggtcaag gccagcggag ccctaactcc tgggtgattc aaatgacgtt aaaaaaagat   1320
atggcggtgg atatcgactc caccaacttc cgccaggcgg ttgcattgtt cgcgacggga   1380
attgcggttc tcagcgcgga gactgaagag ggcgatgtgc acggcatgac cgtgaacagt   1440
ttcacctcca tcagtctgga tccgccgact gtgatggttt ccctgaaatc gggccgtatg   1500
catgagttgc tgactcaagg cggacgcttc ggagttagcc tcttgggtga agccagaag    1560 gtgttctcgg cattcttcag caagcgcgcg atggatgaca cgcctccccc cgccttcacc   1620
attcaggccg gccttcccac tctgcagggc gccatggcct ggttcgaatg cgaggtggag   1680
agcacggttc aagtacacga ccacacgctc ttcattgcgc gcgttagcgc ctgtggaacg   1740
cctgaggcga ataccccccca gccgctgctg ttctttgcca gccgttatca cggcaacccg   1800
ttgccactga attga                                                   1815

<210> SEQ ID NO 6
<211> LENGTH: 510
<212> TYPE: DNA
<213> ORGANISM: Pseudomonas putida

<400> SEQUENCE: 6
atgcttcatg ccttcgaacg caaaatggcc ggccacggca tcctgatgat cttctgcacc     60
cttctatttg tgttggtct ttggatgaac ttggttggcg gctttgaaat catcccggga    120
tacatcatcg agtttcatgt cccgggttcc cctgagggct gggcgagggc tcattccggc    180
cccgcactga atggaatgat ggtgatagca gtggcattcg ttttgcccag ccttggcttc    240
gccgataaga cggcgcgctt gctgggcagc attatcgtcc tggacggttg gtcgaacgtc    300
ggtttctacc ttttctccaa cttctctccc aatcgtggcc tgaccttcgg ccccaaccaa    360
tttgggcctg cgatatcttc agcttcctc gccctggctc ccgcctatct gtttggtgtt    420
ctcgcaatgg gggcgctcgc agtgatcggc taccaggcat tgaagagcac ccgttctcgt    480
aaagctgttc cgcacgctgc tgcggaatga                                    510

<210> SEQ ID NO 7
```

```
<211> LENGTH: 2394
<212> TYPE: DNA
<213> ORGANISM: Pseudomonas putida

<400> SEQUENCE: 7
atgaaaaagc gtatcggtat tgttggtgca ggcactgccg gcctccatct tggtctcttc      60
cttcgtcagc atgacgtcga cgtcactgtg tacactgatc gtaagcccga tgagtacagc     120
ggactgcgtc tcctgaatac cgttgctcac aacgcggtga cggtgcagcg ggaggttgcc     180
ctcgacgtca atgagtggcc gtctgaggag tttggttatt tcggccacta ctactacgta     240
ggtgggccgc agcccatgcg tttctacggt gatctcaagg ctcccagccg tgcagtggac     300
taccgtctct accagccgat gctgatgcgt gcactggaag ccaggggcgg caagttctgc     360
tacgacgcgg tgtctgccga agatctggaa gggctgtcgg agcagtacga tctgctggtt     420
gtgtgcactg gtaaatacgc cctcggcaag gtgttcgaga agcagtccga aaactcgccc     480
ttcgagaagc cgcaacgggc actgtgcgtt ggtctcttca agggcatcaa ggaagcaccg     540
attcgcgcgg tgactatgtc cttctcgcca gggcatggcg agctgattga gattccaacc     600
ctgtcgttca atggcatgag cacagcgctg gtgctcgaaa accatattgg tagcgatctg     660
gaagttctcg cccacaccaa gatgacgat gacccgcgtg cgttcctcga tctgatgctg     720
gagaagctgg gtaagcatca tccttccgtt gccgagcgca tcgatccggc tgagttcgac     780
cttgccaaca gttctctgga catcctccag ggtggtgttg tgccggcatt ccgcgacggt     840
catgcgaccc tcaataacgg caaaaccatc attgggctgg gcgacatcca ggcaactgtc     900
gatccggtct tgggccaggg cgcgaacatg gcgtcctatg cggcatggat ctgggcgag      960 gaaatccttg cgcactctgt ctacgacctg cgcttcagcg aacacctgga gcgtcgccgc    1020
caggatcgcg tgctgtgtgc cacgcgatgg accaacttca ctctgagcgc tctctcggca    1080
cttccgccgg agttcctcgc cttccttcag atcctgagcc agagccgtga atggctgat     1140 gagttcacgg acaacttcaa ctacccggaa cgtcagtggg atcgcttctc cagcccggaa    1200
cgtatcggac agtggtgcag tcagttcgca cccactatcg cggcctgacg ctattgctcc    1260
gctggtcaag gccagcggag ccctaactcc tgggtgattc aaatgacgtt aaaaaaagat    1320
atggcggtgg atatcgactc caccaacttc cgccaggcgg ttgcattgtt cgcgacggga    1380
attgcggttc tcagcgcgga gactgaagag gcgatgtgc acggcatgac cgtgaacagt     1440
ttcacctcca tcagtctgga tccgccgact gtgatggttt ccctgaaatc gggccgtatg    1500
catgagttgc tgactcaagg cggacgcttc ggagttagcc tcttgggtga agccagaag     1560 gtgttctcgg cattcttcag caagcgcgcg atggatgaca cgcctccccc cgccttcacc    1620
attcaggccg gccttcccac tctgcagggc gccatggcct ggttcgaatg cgaggtggag    1680
agcacggttc aagtacacga ccacacgctc ttcattgcgc gcgttagcgc ctgtggaacg    1740
cctgaggcga ataccccca gccgctgctg ttctttgcca gccgttatca cggcaacccg     1800
ttgccactga attgattgcg cacgaacaaa acaacaaaaa ccggtgaggc ctttctgtgc    1860
cgatcaccgg aagaggagat agccatgctt catgccttcg aacgcaaaat ggccggccac    1920
ggcatcctga tgatcttctg cacccttcta tttggtgttg gtctttggat gaacttggtt    1980
ggcggctttg aaatcatccc gggatacatc atcgagtttc atgtcccggg ttcccctgag    2040
ggctgggcga gggctcattc cggccccgca ctgaatggaa tgatggtgat agcagtggca    2100
ttcgttttgc ccagccttgg cttcgccgat aagacgcgc gcttgctggg cagcattatc    2160
gtcctggacg gttggtcgaa cgtcggtttc tacctttct ccaacttctc tcccaatcgt    2220
```

```
ggcctgacct tcggccccaa ccaatttggg cctggcgata tcttcagctt cctcgccctg    2280
gctcccgcct atctgtttgg tgttctcgca atggggcgc tcgcagtgat cggctaccag     2340
gcattgaaga gcacccgttc tcgtaaagct gttccgcacg ctgctgcgga atga          2394
```

<210> SEQ ID NO 8
<211> LENGTH: 38
<212> TYPE: DNA
<213> ORGANISM: Artificial Sequence
<220> FEATURE:
<223> OTHER INFORMATION: PAL2/FDC1 primer for pTpal-fdc

<400> SEQUENCE: 8

```
ggaagatcta ggaggtaacc aatggatcaa atcgaagc                              38
```

<210> SEQ ID NO 9
<211> LENGTH: 33
<212> TYPE: DNA
<213> ORGANISM: Artificial Sequence
<220> FEATURE:
<223> OTHER INFORMATION: PAL2/FDC1 primer for pTpal-fdc

<400> SEQUENCE: 9

```
ttcctcgagc ttctctcatc cgccaaaaca gcc                                   33
```

<210> SEQ ID NO 10
<211> LENGTH: 41
<212> TYPE: DNA
<213> ORGANISM: Artificial Sequence
<220> FEATURE:
<223> OTHER INFORMATION: styABC primer

<400> SEQUENCE: 10

```
atatctagac taggaggcag aacatgaaaa agcgtatcgg t                          41
```

<210> SEQ ID NO 11
<211> LENGTH: 27
<212> TYPE: DNA
<213> ORGANISM: Artificial Sequence
<220> FEATURE:
<223> OTHER INFORMATION: styABC primer

<400> SEQUENCE: 11

```
actaagcttt cattccgcag cagcgtg                                          27
```

<210> SEQ ID NO 12
<211> LENGTH: 37
<212> TYPE: DNA
<213> ORGANISM: Artificial Sequence
<220> FEATURE:
<223> OTHER INFORMATION: PAL2 primer

<400> SEQUENCE: 12

```
tatccatggg cgggaggtaa ccaatggatc aaatcga                               37
```

<210> SEQ ID NO 13
<211> LENGTH: 27
<212> TYPE: DNA
<213> ORGANISM: Artificial Sequence
<220> FEATURE:
<223> OTHER INFORMATION: PAL2 primer

<400> SEQUENCE: 13

```
atttctagat tagcaaatcg gaatcgg                                          27
```

```
<210> SEQ ID NO 14
<211> LENGTH: 43
<212> TYPE: DNA
<213> ORGANISM: Artificial Sequence
<220> FEATURE:
<223> OTHER INFORMATION: FDC1 primer

<400> SEQUENCE: 14
atacctgcag ggggaggaat tatatgagga agctaaatcc agc          43

<210> SEQ ID NO 15
<211> LENGTH: 35
<212> TYPE: DNA
<213> ORGANISM: Artificial Sequence
<220> FEATURE:
<223> OTHER INFORMATION: FDC1 primer

<400> SEQUENCE: 15
attaagcttt tatttatatc cgtacctttt ccaat                    35
```

MICROBIAL PRODUCTION OF 2-PHENYLETHANOL FROM RENEWABLE SUBSTRATES

CROSS-REFERENCE TO RELATED APPLICATIONS

This application represents the national stage entry of PCT International Application No. PCT/US2018/042687, filed Jul. 18, 2018, which claims the benefit of U.S. Patent Application No. 62/536,666, filed Jul. 25, 2017, each of which is incorporated herein by reference as if set forth in its entirety.

STATEMENT REGARDING FEDERALLY SPONSORED RESEARCH

Not applicable.

BACKGROUND

With a 'rose-like' aroma, 2-phenylethanol (2PE) is an important molecule in the flavor and fragrance industries. More specifically, 2PE is used in the production of various foods and beverages and, most notably, remains the most used fragrance compound in the cosmetics and perfume industries. Meanwhile, in addition to its traditional usages as a specialty chemical, 2PE has also garnered recent interest as a potential biofuel molecule due to its low volatility, high energy density and non-hygroscopic properties, or alternatively as a fuel additive helpful for preventing knocking as a result of its high octane number and reduced gas-phase reactivity. Altogether, annual global demand for 2PE exceeds 10,000 tons, with a market size expected to reach $700 million by 2019. Traditional 2PE production methods involve its extraction from the essential oils of many flowering plant species—most notably, rose oil, which contains up to 60% 2PE. Although extraction is still practiced to obtain the natural product, as said process is expensive and poorly scalable, the bulk of 2PE production now instead occurs via its chemical synthesis from petrochemical feedstocks. Though cheaper, 2PE production in such manner is both non-renewable and unsustainable, and furthermore employs carcinogenic precursors (i.e., benzene) as feedstocks; undesirable from a 'green chemistry' perspective and a feature that imposes usage restrictions, especially in flavor/fragrance applications.

In light of the above limitations, microbiological production of 2PE via a variety of synthesis routes has recently been explored as a more sustainable alternative. A natural fermentation product of several yeast strains (albeit typically at only trace levels), 2PE is in large part responsible for the 'floral' aromas present in many fermented foods and beverages (Kieser et al., 1964; Lee and Richard, 1984). In yeast, 2PE is produced via the Ehrlich pathway (Ehrlich, *Berichte der Dtsch. Chem. Gesellschaft* 40:1027-1047, 1907; Hazelwood et al., *Appl. Environ. Microbiol.* 74:2259-2266 (2008)); a two-step pathway stemming from phenylpyruvate, an intermediate of the shikimic acid (SA) pathway and precursor to L-phenylalanine (Phe). First, phenylpyruvate decarboxylase (PPDC) serves to convert phenylpyruvate to 2-phenylacetaldehyde which is subsequently reduced to 2PE by an alcohol dehydrogenase (FIG. 1). In *Saccharomyces cerevisiae*, for example, ARO10 catalyzes the first step whereas reduction of 2-phenylacetaldehyde to 2PE occurs by the aid of one or more native dehydrogenases (including ADH1-5) (Dickinson et al., *J. Biol. Chem.* 278:8028-34 (2003)). Achieving high levels of 2PE via their native Ehrlich pathway, however, typically requires select yeast strains (e.g., *S. cerevisiae, Kluyveromyces marxianus*) to be cultured under nitrogen limited conditions while supplementing the medium with excess exogenous phenylalanine (note: phenylalanine transaminase (e.g., ARO9 in *S. cerevisiae*) converts phenylalanine and 2-ketoglutarate to phenylpyruvate and L-glutamate, the latter then being degraded to provide nitrogen for growth). However, as phenylalanine is an expensive and poorly scalable feedstock, 2PE production directly from renewable biomass sugars represents a more promising approach.

To date, microbial 2PE production from glucose has focused predominantly on expanded applications of the Ehrlich pathway, most commonly via its functional reconstruction in other, heterologous microbes. For example, Atsumi et al. (*Nature* 451:86-9 (2008)) first reported the functional reconstruction of the Ehrlich pathway in *Escherichia coli* (comprised of kivd from *Lactococcus lactis* and ADH2 from *S. cerevisiae*), demonstrating production of 57.3 mg/L 2PE from 36 g/L glucose (a yield of 1.59 mg/g) using a wild-type background (Atsumi et al., 2008). Kang et al. (*Appl. Biochem. Biotechnol.* 172:2012-21 (2014)) later also reconstructed the Ehrlich pathway in *E. coli* (in this case instead using kdc and ADH1 from *Pichia pastoris* and *S. cerevisiae*, respectively) and, following deregulation of metabolite flux through the SA pathway, reported 2PE titers as high as 285 mg/L (Kang et al., 2014). Finally, expressing the Ehrlich pathway composed instead of ipdC from *Azospirillum brasilense* and yahK from *E. coli* in a phenylalanine over-producing host, Koma et al. (*Appl. Environ. Microbiol.* 78:6203-6216 (2012)) engineered *E. coli* for direct 2PE production from glucose at titers reaching 940.6 mg/L and a yield of 94.06 mg/g (Koma et al., 2012). However, functional reconstruction of the Ehrlich pathway in *E. coli* has its limitations and further work is needed to improve biosynthetic production of 2PE.

SUMMARY

In a first aspect, provided herein is a recombinant organism comprising (i) at least one heterologous gene encoding an enzyme having phenylalanine ammonia lyase (PAL) activity, (ii) at least one heterologous gene encoding an enzyme having trans-cinnamic acid decarboxylase (CADC) activity, (iii) at least one heterologous gene encoding an enzyme having styrene monooxygenase (SMO) activity, (iv) at least one heterologous gene encoding an enzyme having styrene oxide isomerase (SOI) activity, and (v) at least one gene encoding an enzyme having 2-phenylacetaldehyde reductase (PAR) activity, wherein the recombinant microorganism is capable of producing 2-phenylethanol from a fermentable carbon substrate. The organism can be *Escherichia coli*. The organism can be a phenylalanine overproducing strain of *E. coli*. The gene encoding a polypeptide having phenylalanine ammonia lyase activity can be derived from *Arabidopsis thaliana*. The gene encoding polypeptides having trans-cinnamic acid decarboxylase activity can be derived from *Saccharomyces cerevisiae*. The gene encoding a polypeptide having styrene monooxygenase activity can be derived from *Pseudomonas putida*. The gene encoding a polypeptide having styrene oxide isomerase activity can be derived from *Pseudomonas putida*.

In another aspect, provided herein is a method of producing 2-phenylethanol comprising the steps of (i) contacting a recombinant organism engineered to produce 2-phenylethanol with a fermentable carbon substrate, and (ii) growing the recombinant organism for a time sufficient to produce 2-phenylethanol. The fermentable carbon substrate can be selected from the group consisting of monosaccharides, oligosaccharides, polysaccharides, glycerol, carbon dioxide, methanol, methane, formaldehyde, formate, amino acids, and carbon-containing amines. The fermentable carbon source can be glucose, xylose, or glycerol. The fermentable carbon substrate is selected from the group consisting of lignin-derived aromatic monomers, lignin-derived aromatic oligomers, and combinations thereof. The fermentable carbon source can be a biomass hydrolysate.

In a further aspect, provided herein is a recombinant organism comprising, (i) at least one heterologous gene encoding an enzyme having phenylalanine ammonia lyase (PAL) activity, (ii) at least one heterologous gene encoding an enzyme having trans-cinnamic acid decarboxylase (CADC) activity, (iii) at least one heterologous gene encoding an enzyme having styrene monooxygenase (SMO) activity, (iv) at least one heterologous gene encoding an enzyme having styrene oxide isomerase (SOI) activity, and (v) at least one gene encoding an enzyme having 2-phenylacetaldehyde dehydrogenase (PADH) activity, wherein the engineered microorganism is capable of producing 2-phenylacetic acid from a fermentable carbon substrate. The organism can be *Escherichia coli*. The organism can be a phenylalanine overproducing strain of *E. coli*. The gene encoding a polypeptide having phenylalanine ammonia lyase activity can be derived from *Arabidopsis thaliana*. The gene encoding polypeptides having trans-cinnamic acid decarboxylase activity can be derived from *Saccharomyces cerevisiae*. The gene encoding a polypeptide having styrene monooxygenase activity can be derived from *Pseudomonas putida*. The gene encoding a polypeptide having styrene oxide isomerase activity can be derived from *Pseudomonas putida*.

In another aspect, provided herein is a method of producing 2-phenylacetic acid comprising the steps of (i) contacting a recombinant organism engineered to produce 2-phenylacetic acid with a fermentable carbon substrate, and (ii) growing the recombinant organism for a time sufficient to produce 2-phenylacetic acid. The fermentable carbon substrate can be selected from the group consisting of monosaccharides, oligosaccharides, polysaccharides, glycerol, carbon dioxide, methanol, methane, formaldehyde, formate, amino acids, carbon-containing amines. The fermentable carbon source can be selected from the group consisting of glucose, xylose, or glycerol. The fermentable carbon substrate is selected from the group consisting of lignin-derived aromatic monomers, lignin-derived aromatic oligomers, and combinations thereof. The fermentable carbon source can be a biomass hydrolysate.

Although the following description refers to certain aspects or embodiments, such aspects or embodiments are illustrative and non-exhaustive in nature. Having reviewed the present disclosure, persons of ordinary skill in the art will readily recognize and appreciate that numerous other possible variations or alternative configurations or aspects are possible and were contemplated within the scope of the present disclosure. Accordingly, the detailed descriptions are to be regarded as illustrative in nature and not restrictive.

Figure 1:
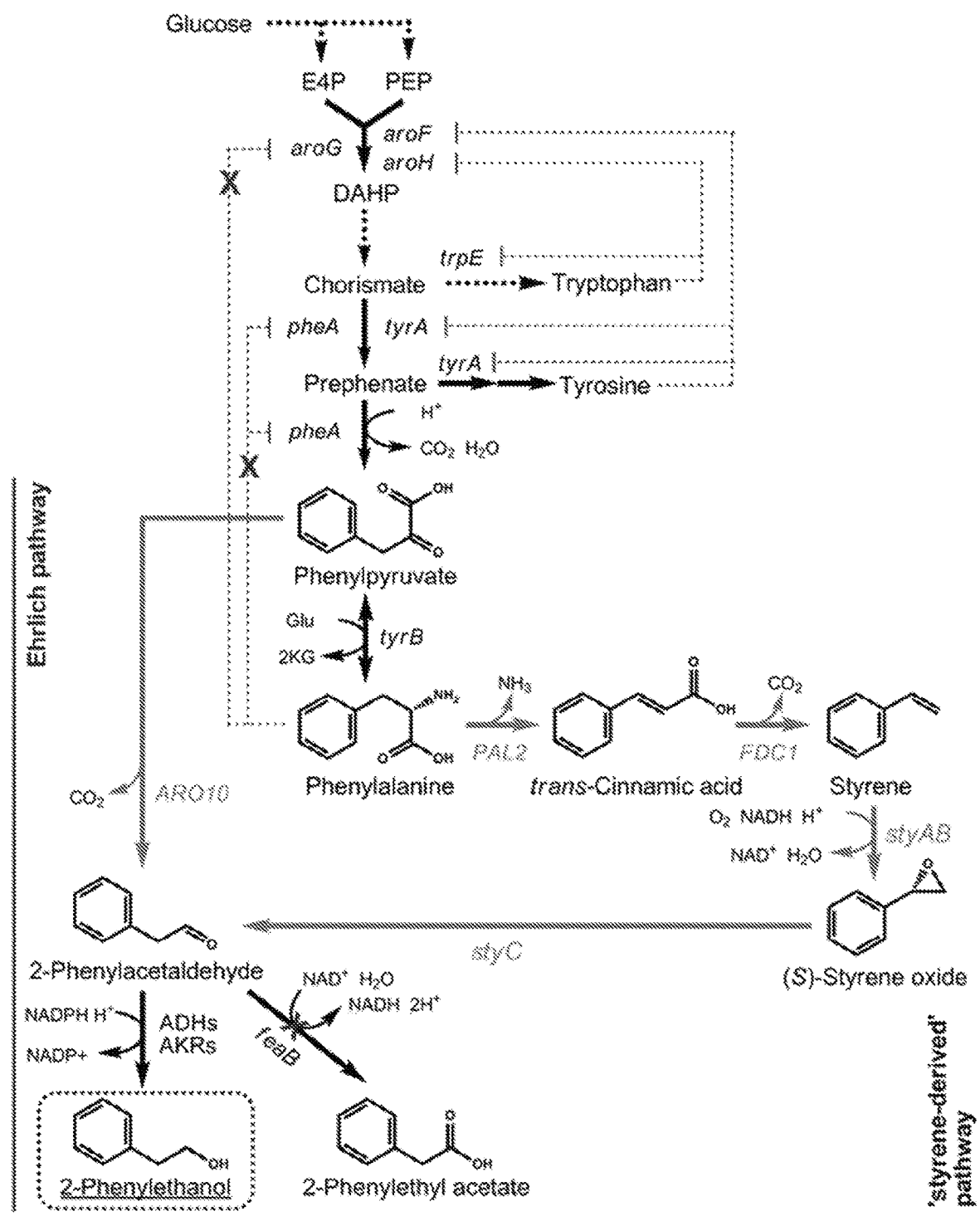
FIG. 1 shows a comparison of 2PE biosynthesis via the established Ehrlich and proposed styrene-derived pathways. Endogenous pathway steps shown with black arrows whereas heterologous steps are shown in gray.

styrene oxide isomerase (SOI), and v) 2-phenylacetaldehyde reductase (PAR); and, (B) 2-phenylacetic acid composed of i) phenylalanine ammonia lyase (PAL), ii) trans-cinnamic acid decarboxylase (CADC), iii) styrene monooxygenase (SMO), iv) styrene oxide isomerase (SOI), and v) 2-phenylacetaldehyde dehydrogenase (PADH).

INCORPORATION BY REFERENCE

All publications, including but not limited to patents and patent applications, cited in this specification are herein incorporated by reference as though set forth in their entirety in the present application.

DETAILED DESCRIPTION

The present disclosure describes microorganisms engineered to produce 2-phenylethanol and/or 2-phenylacetic acid from renewable carbon sources. The recombinant microorganisms described herein are based at least in part on the inventors' development of engineered enzyme pathways for the microbial biosynthesis of 2-phenylethanol and 2-phenylacetic acid from renewable biomass resources in the bacterium Escherichia coli (E. coli). The pathways uniquely proceed from L-phenylalanine as the immediate endogenous precursor. The pathways uniquely include trans-cinnamate, styrene, and/or (S)-styrene oxide as intermediate precursors.

Recombinant host microorganisms are engineered to produce 2-phenylethanol and/or 2-phenylacetic acid from L-phenylalanine via an enzymatic pathway comprising heterologous enzymes with phenylalanine ammonia lyase, trans-cinnamic acid decarboxylase, styrene monooxygenase, and styrene oxide isomerase activity and at least one enzyme with 2-phenylacetaldehyde reductase activity or 2-phenylacetaldehyde dehydrogenase activity. In another aspect, the present invention describes methods of producing 2-phenylethanol or 2-phenylacetic acid using the engineered microorganisms described herein.

In some aspects, an engineered microorganism provided herein will comprise the complete biosynthetic pathway required for the conversion of L-phenylalanine to 2-phenylethanol. The host microorganism will comprise an enzyme having phenylalanine ammonia lyase activity, an enzyme having trans-cinnamic acid decarboxylase activity, an enzyme having styrene monooxygenase activity, an enzyme having styrene oxide isomerase activity and an enzyme with 2-phenylacetaldehyde reductase activity. Portions of the pathway have previously been described in U.S. Pat. No. 9,150,884, which is incorporated herein by reference.

In some aspects, an engineered microorganism provided herein will comprise the complete biosynthetic pathway required for the conversion of L-phenylalanine to 2-phenylacetic acid. The host microorganism will comprise an enzyme having phenylalanine ammonia lyase activity, an enzyme having trans-cinnamic acid decarboxylase activity, an enzyme having styrene monooxygenase activity, an enzyme having styrene oxide isomerase activity and an enzyme with 2-phenylacetaldehyde dehydrogenase activity. Portions of the pathway have previously been described in U.S. Pat. No. 9,150,884, which is incorporated herein by reference.

The term "host" refers to a suitable organism or cell line such as a strain of bacteria, for example, into which genes can be transferred to impart desired genetic attributes and functions. The host organisms of the present invention will include any organism capable of expressing the genes required for 2-phenylethanol or 2-phenylacetic acid production. Typically, the host organism will be restricted to microorganisms or plants. Microorganisms useful in the present invention include, but are not limited to enteric bacteria (Escherichia and Salmonella, for example) as well as Bacillus, Sphingomonas, Clostridium, Acinetobacter, Actinomycetes such as Streptomyces, Corynebacterium; methanotrophs such as Methylosinus, Methylomonas, Rhodococcus and Pseudomonas; cyanobacteria, such as Synechococcus and Synechocystis; yeasts, such as Saccharomyces, Zygosaccharomyces, Kluyveromyces, Candida, Hansenula, Debaryomyces, Mucor, Pichia, Yarrowia, and Torulopsis; filamentous fungi, such as Aspergillus and Arthrobotrys; and algae, such as Chlamydomonas, for example. The genes encoding polypeptides with the PAL, CADC, SMO, SOI, PAR and PADH activities used in the present invention may be native to or introduced in these and other microbial hosts and expressed or over-expressed to prepare large quantities of 2-phenylethanol or 2-phenylacetic acid.

Microbial expression systems and expression vectors containing regulatory sequences that direct high-level expression of foreign proteins and overexpression of native proteins are well known to those skilled in the art. Any of these could be used to construct chimeric genes for the production of 2-phenylethanol or 2-phenylacetic acid. These chimeric genes could then be introduced into appropriate microorganisms via transformation to allow for expression of high levels of the enzymes.

Although any of the above mentioned microorganisms would be useful for the production of 2-phenylethanol or 2-phenylacetic acid, preferred strains would be those that either natively or have been engineered to over-produce phenylalanine. Phenylalanine over-producing strains are known and include, but are not limited to, Escherichia sp., Corynebacterium sp., Microbacterium sp., Arthrobacter sp., Pseudomonas sp., and Brevibacteria sp. Particularly useful phenylalanine over-producing strains include, but are not limited to, Microbacterium ammoniaphilum ATCC 10155, Corynebacterium lillium NRRL-B-2243, Corynebacterium glutamicum ATCC 21674, E. coli NST74, E. coli NST37, and Arthrobacter citreus ATCC 11624. A recombinant host may be constructed from a suitable phenylalanine overproducing strain such that it expresses at least one gene encoding a polypeptide having PAL, at least one gene encoding a polypeptide having CADC activity, at least one gene encoding a polypeptide having SMO activity, at least one gene encoding a polypeptide having SOI activity, and at least one gene encoding a polypeptide having PAR or PADH activity.

The term "phenylalanine over-producing strain" refers to a microbial strain that produces endogenous levels of phenylalanine that are significantly higher than those demonstrated by the wild-type of that strain. Specific examples of E. coli phenylalanine over-producing strains are NST74 and NST37 (U.S. Pat. No. 4,681,852). Meanwhile, still others may include specific strains of Corynebacterium glutamicum (U.S. Pat. No. 3,660,235).

As used herein, "phenylalanine ammonia lyase (PAL)" refers to an enzyme that catalyzes the conversion of L-phenylalanine to trans-cinnamic acid. The term encompasses wild type or naturally occurring phenylalanine ammonia lyase, as well as functional fragments or variants of a wild type phenylalanine ammonia lyase. Genes encoding PAL activity are known in the art and several have been sequenced from both microbial and plant origin (see, for example, EP 321488 [R. toruoides]; WO 9811205 [Eucalyptis grandis and Pinus radiata]; WO 9732023 [Petunia];

JP 05153978 [*Pisum sativum*]; WO 9307270 [potato, rice]; NM_129260.2 GI:30687012 and NM_115186.3 GI:42565889 [*Arabdiposis thaliana*]). The sequence of PAL encoding genes are available (for example, see GenBank AJ010143 and X75967). Where expression of a wild type PAL in a recombinant host is desired, the wild type gene may be obtained from any source including, but not limited to, yeasts such as *Rhodotorula* sp., *Rhodosporidium* sp., and *Sporobolomyces* sp.; bacteria such as *Streptomyces* sp., *Anabaena* sp., and *Nostoc* sp.; and plants such as pea, potato, rice, *eucalyptus*, pine, corn, *petunia, Arabidopsis*, tobacco, and parsley. It is preferred, but not necessary, that enzymes should strictly display PAL activity and not TAL activity as well. In one embodiment, the phenylalanine ammonia lyase is PAL2 from *Arabidopsis thaliana* (SEQ ID NO:1).

As used herein, "trans-cinnamic acid decarboxylase (CADC)" refers to an enzyme that catalyzes the conversion of trans-cinnamic acid to styrene. The term encompasses wild type or naturally occurring trans-cinnamic acid decarboxylase, as well as functional fragments or variants of a wild type trans-cinnamic acid decarboxylase. Genes which encode trans-cinnamic acid decarboxylase (CADC) activity have been identified in the literature. In addition, enzymes which have been classified as phenylacrylic acid decarboxylase (PADC) or ferulic acid decarboxylase (FADC) may also display the necessary CADC activity. Genes encoding PADC activity, for example, have been isolated from the bacteria *Lactobacillus plantarum* (AAC45282.1 GI:1762616), *Lactococcus lactis* (NP_268087.1 GI:15673912), and *Bacillus subtilis* (AF017117.1 GI:2394281). Furthermore, CADC activity has been reported in the yeast *Saccharomyces cerevisiae* and it was shown that the display of this native activity required that the genes PAD1 (L09263.1 GI:393284) and FDC1 (NP_010828.1 GI:6320748) both be present and undisturbed in the genome. Genomic disruption of either PAD1 or FDC1 resulted in the loss of CADC activity upon exogenously supplied trans-cinnamic acid. In *E. coli*, expression of FDC1 alone may be sufficient for conferring trans-cinnamic acid decarboxylase (CADC) activity. Without being bound to any particular theory, this is believed to be due to the complementary function of native ubiX, a known homolog of PAD1. Considering the structural similarity between ferulic acid and trans-cinnamic acid, we expect that enzymes which are known to display ferulic acid decarboxylase (FADC) activity, such as the polypeptide encoded by FDC1 of *S. cerevisiae*, may also display trans-cinnamic acid decarboxylase (CADC) activity as well. In one embodiment, the trans-cinnamic acid decarboxylase is FDC1 from *S. cerevisiae* (SEQ ID NO:2).

As used herein, "styrene monooxygenase (SMO)" refers to an enzyme that catalyzes the conversion of styrene to (S)-styrene oxide. The term encompasses wild type or naturally occurring styrene monooxygenase, as well as functional fragments or variants of a wild type styrene monooxygenase. Genes which encode styrene monooxygenase activity have been identified in the literature. In addition, enzymes which have been classified as an alkene monooxygenase may also display the necessary SMO activity. Genes encoding SMO activity, for example, have been isolated from *Pseudomonas fluorescens* (Z92524.1 GI:2154926). Furthermore, SMO activity has been reported in *Rhodococcus opacus* ADP1, *Rhodococcus opacus* 1CP, *Rhodococcus* sp. AD45, and *Pseudomonas* sp. strain VLB120. In some embodiments, styrene monooxygenase may be composed of a single protein subunit. In some embodiments, styrene monooxygenase may be a multi-subunit protein. In one embodiment, the styrene monooxygenase is comprised of both monooxygenase and reductase subunits, encoded by the individual genes styA (SEQ ID NO:3) and styB (SEQ ID NO:4) from *Pseudomonas putida* S12, respectively. In one embodiment, the styrene monooxygenase is comprised of the native gene cluster styAB from *P. putida* S12 (SEQ ID NO:5).

As used herein, "styrene oxide isomerase (SOI)" refers to an enzyme that catalyzes the conversion of (S)-styrene oxide to 2-phenylacetaldehyde. The term encompasses wild type or naturally occurring styrene oxide isomerase, as well as functional fragments or variants of a wild type styrene oxide isomerase. In some embodiments the styrene oxide isomerase is heterologous to the host microorganism. Genes which encode styrene oxide isomerase activity have been identified in the literature. Genes encoding SOI activity, for example, have been isolated from *Metarhizium majus* (MAJ_11235 GI:26280817) and *Pseudomonas fluorescens* (Z92524.1 GI:2154926). Furthermore, SOI activity has been reported in *Rhodococcus opacus, Rhodococcus opacus* 1CP, *Corynebacterium* sp., *Xanthobacter* sp., *Pseudomonas* sp. strain VLB120, and *Pseudomonas putida* CA-3. In one embodiment, the styrene oxide isomerase is styC from *P. putida* S12 (SEQ ID NO:6). In one embodiment, the styrene monooxygenase and styrene oxide isomerase are comprised of the native operon styABC from *P. putida* S12 (SEQ ID NO:7).

As used herein, "2-phenylacetaldehyde reductase (PAR)" refers to an enzyme that catalyzes the conversion of 2-phenylacetaldehyde to 2-phenylethanol. The term encompasses wild type or naturally occurring 2-phenylacetaldehyde reductase, as well as functional fragments or variants of a wild type 2-phenylacetaldehyde reductase. Genes which encode 2-phenylacetaldehyde reductase activity have been identified in the literature. In addition, enzymes which have been classified as aldo-keto reductases and alcohol dehydrogenases may also display the necessary PAR activity. Genes encoding PAR activity, for example, have been isolated from *Solanum lycopersicum* (NC 015438.2 GI:100134901). Furthermore, PAR activity has been reported in *S. cerevisiae, Rosa hybrid cultivar, Petunia* x *hybrid*. In some embodiments, an enzyme or a gene encoding an enzyme with PAR activity is native to the host organism. In some embodiments, the PAR enzyme is heterologous to the host organism. In some embodiments, the PAR is selected from the group consisting of dkgA (NC 000913.3 GI:948543), dkgB (NC_000913.3 GI:944901), and yeaE (NC_000913.3 GI:946302) from *E. coli*.

As used herein, "2-phenylacetaldehyde dehydrogenase (PADH)" refers to an enzyme that catalyzes the conversion of 2-phenylacetaldehyde to 2-phenylacetic acid. The term encompasses wild type or naturally occurring 2-phenylacetaldehyde dehydrogenase, as well as functional fragments or variants of a wild type 2-phenylacetaldehyde dehydrogenase. Genes which encode 2-phenylacetaldehyde dehydrogenase activity have been identified in the literature. In addition, enzymes which have been classified as aldehyde dehydrogenase may also display the necessary PADH activity. Genes encoding PADH activity, for example, have been isolated from *Pseudomonas putida* KT2440 (NC_002947.4 GI:1046275), *Salmonella enterica* (NC_003197.2 GI:1254652), *Acinetobacter pittii* (NC_016603.1 GI:11639512), *Klebsiella pneumoniae* (NC_016845.1 GI:11847382), and *Pseudomonas fluorescens* (Z92524.1 GI:2154926). Furthermore, PADH activity has been reported in *Brevibacterium* sp., *Xanthobacter* sp., and *Flavobacterium* sp. In some embodiments, an enzyme or a gene encoding an enzyme with PADH activity is native to the host organism. In some embodiments, the PADH enzyme is heterologous to the host organism. In one embodiment, the PADH enzyme is encoded by feaB (NC_000913.3 GI:945933) from *E. coli*.

It is also envisioned that native genes encoding enzymes with PAR or PADH activity may be downregulated, silenced, eliminated or mutated in the host organism to reduce or eliminate their inherent net and/or specific activity and direct the products of the biosynthetic pathway to either 2-phenylethanol or 2-phenylacetic acid, as appropriate. As 2-phenylethanol is produced from 2-phenylacetaldehyde by an enzyme with PAR activity or 2-phenylacetic acid is produced from 2-phenylacetaldehyde by an enzyme with PADH activity, deletion of one or more genes encoding enzymes with PAR activity will push the products of the reaction to 2-phenylacteic acid and deletion of one or more genes encoding enzymes with PADH activity will push the products of the reaction to 2-phenylethanol. In some embodiment, one or more genes encoding enzymes with PADH activity are deleted form the host organism. In some embodiments, a host organism lacking a gene encoding an enzyme with PADH activity is selected. In some embodiments, one or more genes encoding enzymes with PAR activity are deleted from the host organism. In some embodiments, a host organism lacking a gene encoding an enzyme with PAR activity is selected.

It is also envisioned that native genes encoding enzymes with PAR or PADH activity may be upregulated or mutated in the host organism to increase their inherent net and/or specific activity and direct the products of the biosynthetic pathway to either 2-phenylethanol or 2-phenylacetic acid, as appropriate. As 2-phenylethanol is produced from 2-phenylacetaldehyde by an enzyme with PAR activity or 2-phenylacetic acid is produced from 2-phenylacetaldehyde by an enzyme with PADH activity, upregulation of one or more genes encoding native enzymes with PAR activity will push the products of the reaction to 2-phenylethanol and upregulation of one or more native genes encoding enzymes with PADH activity will push the products of the reaction to 2-phenylacetic acid. In some embodiments, one or more native genes encoding enzymes with PAR activity are upregulated in the host organism. In some embodiments, one or more native genes encoding enzymes with PADH activity are upregulated in the host organism.

As used herein, the term "heterologous" refers to any biological entity such as, but not limited to, DNA, RNA, proteins, enzymes, polypeptides, antibodies, and the like, that are not naturally occurring in the host cell or host organism. Heterologous genes or proteins are those that have been derived from a different organism or species than the host organism into which they are introduced.

It will be appreciated that the present disclosure is not limited to the genes encoding polypeptides having the specific activities mentioned above, but will encompass any suitable homologs of such genes that may be obtained by standard methods. Methods of obtaining homologs to these genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR)).

For example, genes encoding homologs of the polypeptides that alone or in combination have the above mentioned activities could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art. Moreover, the entire sequences can be used directly to synthesize DNA probes by methods known to those skilled in the art, such as random primers DNA labeling, nick translation, or end-labeling techniques or RNA probes using available in vitro transcription systems. In addition, specific primers can be designed and used to amplify a part of or full length of the instant sequences. The resulting amplification products can be labeled directly during amplification reactions or labeled after amplification reactions, and used as probes to isolate full-length cDNA or genomic fragments under conditions of appropriate stringency.

The term "gene" refers to a nucleic acid fragment that expresses a specific protein, including regulatory sequences preceding (5' non-coding sequences) and following (3' non-coding sequences) and the coding sequence. "Native gene" or "wild type gene" refers to a gene as found in nature with its own regulatory sequences. "Endogenous gene" refers to a native gene in its natural location in the genome of an organism. "Foreign gene" refers to a gene not normally found in the host organism but that is introduced into the host organism by gene transfer. Foreign genes can comprise native genes inserted into a non-native organism, or chimeric genes.

The term "expression", as used herein, refers to the transcription and stable accumulation of sense (mRNA) or antisense RNA derived from the nucleic acid fragment used in this invention. Expression may also refer to the translation of the mRNA into a polypeptide. "Over-expression" refers to the production of a gene product in a transgenic organism that exceeds levels of production in the wild-type host or native organisms.

"RNA transcript" refers to the product resulting from RNA polymerase-catalyzed transcription of gene or other a DNA sequence. "Messenger RNA (mRNA)" refers to the RNA that is without introns and can be translated into a protein by the cell. As used herein, the term "cDNA" refers to double-stranded DNA that is complimentary to and derived from mRNA. "Sense" RNA refers to RNA transcript that includes the mRNA and so can be translated into protein by the cell.

As used herein, the term "recombinant" refers to a biomolecule that has been manipulated in vitro, e.g., using recombinant DNA technology to introduce changes to a genome. Introducing such changes to a genome can be achieved by transformation. As used herein, the term "transformation" refers to the transfer of a nucleic acid fragment into the genome of the host organism, resulting in genetically-stable inheritance. Host organisms containing the transformed nucleic acid fragments are referred to as "transgenic" or "recombinant" or "transformed" organisms.

The terms "plasmid" and "vector" refer to an extra chromosomal genetic element often carrying genes which are not part of host native genome nor the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The methods of producing 2-phenylethanol and 2-phenylacetic acid described herein involves the incorporation of genes encoding polypeptides displaying PAL, CADC, SMO, SOI, and PAR or PADH activities into a single host organism and the use of those organisms to convert renewable resources, including fermentable carbons sources such as glucose, for example, to 2-phenylethanol or 2-phenylacetic acid.

Figures 10A, 10B:
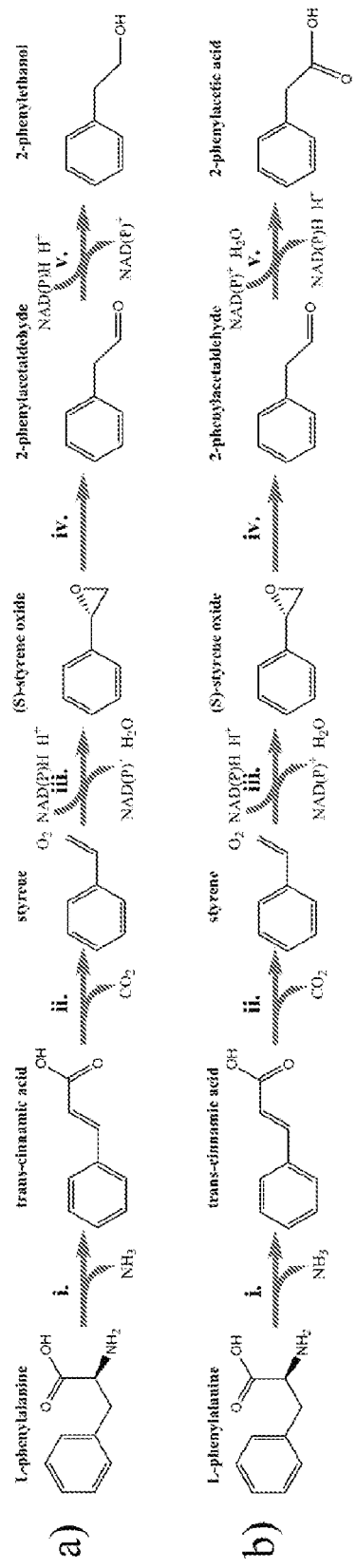
FIGS. 10A-10B show the enzymatic pathway for the biosynthesis of (A) 2-phenylethanol composed of i) phenylalanine ammonia lyase (PAL), ii) trans-cinnamic acid decarboxylase (CADC), iii) styrene monooxygenase (SMO), iv)

In some aspects, the present invention comprises an in vivo method for the production of 2-phenylethanol via a recombinant organism co-expressing at least one gene encoding a polypeptide having phenylalanine ammonia lyase (PAL) activity to convert endogenously-synthesized L-phenylalanine to trans-cinnamic acid, at least one gene encoding a polypeptide having trans-cinnamic acid decarboxylase (CADC) activity to convert trans-cinnamic acid to styrene, at least one gene encoding a polypeptide having styrene monooxygenase (SMO) activity to convert styrene to (S)-styrene oxide, at least one gene encoding a polypeptide having styrene oxide isomerase (SOI) activity to convert (S)-styrene oxide to 2-phenylacetaldehyde, and at least one gene encoding a polypeptide having 2-phenylacetaldehyde reductase (PAR) activity to convert 2-phenylacetaldehyde to 2-phenylethanol. The reaction schemes are illustrated in FIG. 10A. The recombinant organism is grown on a fermentable carbon substrate under conditions and for a time suitable to produce 2-phenylenthanol.

In some aspects, provided herein is an in vivo method for the production of 2-phenylacetic acid via a recombinant organism co-expressing at least one gene encoding a polypeptide having phenylalanine ammonia lyase (PAL) activity to convert endogenously-synthesized L-phenylalanine to trans-cinnamic acid, at least one gene encoding a polypeptide having trans-cinnamic acid decarboxylase (CADC) activity to convert trans-cinnamic acid to styrene, at least one gene encoding a polypeptide having styrene monooxygenase (SMO) activity to convert styrene to (S)-styrene oxide, at least one gene encoding a polypeptide having styrene oxide isomerase (SOI) activity to convert (S)-styrene oxide to 2-phenylacetaldehyde, and at least one gene encoding a polypeptide having 2-phenylacetaldehyde dehydrogenase (PADH) activity to convert 2-phenylacetaldehyde to 2-phenylacetic acid. This reaction scheme is illustrated in FIG. 10B. The recombinant organism is grown on a fermentable carbon substrate under conditions and for a time suitable to produce 2-phenylacetic acid.

Growth of the recombinant organism can be carried out in suitable medium and for a suitable time to produce the desired products. For example, seed cultures may be grown in 3 mL LB broth supplemented with appropriate antibiotics at 32° C. for 12-16 h. Next, 0.5 mL of seed culture may be used to inoculate 50 mL (in 250 mL shake flasks) of pH 6.8 MM1 media, with the following recipe (in g/L): glucose (20), $MgSO_4 \cdot 7H_2O$ (0.5), $(NH_4)_2SO_4$ (4.0), MOPS (24.7), $KH_2PO_4$ (0.3), and $K_2HPO_4$ (1.0), as well as 1 mL/L of a trace mineral solution containing (in g/L): Thiamine HCl (0.101), $MnCl_2 \cdot 4H_2O$ (1.584), $ZnSO_4 \cdot 7H_2O$ (0.288), $CoCl_2 \cdot 6H_2O$ (0.714), $CuSO_4$ (0.1596), $H_3BO_3$ (2.48), $(NH_4)_6Mo_7O_{24} \cdot 4H_2O$ (0.370), and $FeCl_3$ (0.050). Once inoculated, cultures may be grown at 32° C. while shaking at 200 RPM until reaching an $OD_{600}$ of 0.8 (~8 h), at which time they may be induced by addition of IPTG at a final concentration of 0.2 mM. Following induction, strains may be cultured for a total of 72 h. Intermittently throughout each culture, pH may be increased back to its initial value by adding a minimal volume (typically ~0.2-0.4 mL) of 0.4 g/L $K_2HPO_4$ solution.

The recombinant organism may be grown in the any system known in the art suitable for the grown and propagation of the host organism. Suitable growth systems include, but are not limited to, shaker flasks, incubators, fermenters, bioreactors, batch bioreactors, fed-batch bioreactors, continuous bioreactors, immobilized cell bioreactors, airlift bioreactors, and the like.

The term "fermentable carbon substrate" refers to a carbon source capable of being metabolized by the host organisms of the present invention and particularly carbon sources selected from the group consisting of monosaccharides, oligosaccharides, polysaccharides, organic acids, glycerol, and one-carbon substrates or mixtures thereof. In some embodiment, the fermentable carbon substrate is derived from a renewable biomass feedstock.

As used herein, the term "renewable biomass feedstock" refers to any renewable biological material, living or recently dead and any byproduct of those organisms, plant or animal. As used herein, the term "biomass" refers to, without limitation, organic materials produced by plants (such as leaves, roots, seeds and stalks), and microbial and animal metabolic wastes. Common biomass sources include: (1) agricultural residues, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; (4) algae-derived biomass, including carbohydrates and lipids from microalgae (e.g., *Botryococcus braunii*, *Chlorella*, *Dunaliella tertiolecta*, *Gracilaria*, *Pleurochyrsis carterae*, and *Sargassum*) and macroalgae (e.g., seaweed); and (5) energy crops, such as poplars, willows, switch grass, *miscanthus*, sorghum, alfalfa, prairie bluestream, corn, soybean, and the like. The term also refers to the primary building blocks of the above—lignin, cellulose, hemicellulose, carbohydrates, etc. Prior to use in the methods of the present invention biomass may be processed by any means known in the art to produce a fermentable carbon source suitable for use in the present invention. In some embodiments, the fermentable carbon source is a biomass hydrolysate. The term "biomass hydrolysate" refers to the product resulting from saccharification of biomass such as lignocellulosic biomass. In some cases, the biomass is pretreated or preprocessed prior to saccharification, and saccharified enzymatically. In some embodiments, the fermentable carbon source is derived from lignin. In some embodiments, the fermentable carbon source comprises mixtures of lignin-derived aromatic monomers and/or lignin derived aromatic oligomers.

The 2-phenylethanol and 2-phenylacetic acid produced by the methods described herein can be recovered by any suitable means known in the art. Examples of separation methods that can be used to separate 2-phenylethanol and/or 2-phenylacetic acid from culture media include but are not limited to solvent extraction, perstraction, gas stripping, vacuum stripping, pervaporation, adsorption, ion exchange adsorption, precipitation, and the like.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, MOLECULAR CLONING: A LABORATORY MANUAL, second edition (Sambrook et al., 1989) Cold Spring Harbor Laboratory Press; CURRENT PROTOCOLS IN MOLECULAR BIOLOGY (F. M. Ausubel et al., eds., 1987 and annual updates); OLIGONUCLEOTIDE SYN- THESIS (M. J. Gait, ed., 1984); PCR: THE POLYMERASE CHAIN REACTION, (Mullis et al., eds., 1994); and MANUAL OF INDUSTRIAL MICROBIOLOGY AND BIOTECHNOLOGY, Second Edition (A. L. Demain, et al., eds. 1999).

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The indefinite articles "a" and "an," as used herein in the specification and in the claims, unless clearly indicated to the contrary, should be understood to mean "at least one."

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

The present invention has been described in terms of one or more preferred embodiments, and it should be appreciated that many equivalents, alternatives, variations, and modifications, aside from those expressly stated, are possible and within the scope of the invention.

EXAMPLES

Example 1

The embodiments described here demonstrate the production of 2-phenylethanol and 2-phenylacetic acid in engineered microorganisms via the heterologous metabolic pathways described herein.

Materials and Methods

Microorganisms.

All strains used in this study are listed in Table 1. *E. coli* NEB 10-beta was obtained from New England Biolabs (NEB; Ipswich, Mass.) and was used for cloning and the propagation of all plasmids. *E. coli* NST74 (ATCC 31884), a feedback resistant mutant of *E. coli* which overproduces Phe (Tribe, 1987), *P. putida* S12 (ATCC 700801), which served as the genetic source of styAB, styC, and styABC, and *S. cerevisiae* W303 (ATCC 200060), which served as the genetic source of ARO10 were all purchased from the American Type Culture Collection (ATCC; Manassas, Va.). *E. coli* strains JW1380-1, JW1843-2, JW1666-3, and JW2410-1 were obtained from the *Coli* Genetic Stock Center (CGSC; New Haven, Conn.) and served as the genetic source for the feaB::FRT-kan$^R$-FRT, pykA::FRT-kan$^R$-FRT, pykF::FRT-kan$^R$-FRT, and crr::FRT-kan$^R$-FRT deletion cassettes, respectively, along with wild-type *E. coli* BW25113. Chromosomal in-frame gene deletions in *E. coli* and subsequent kan$^R$ marker removal were accomplished via a method modified from that of Datsenko and Wanner (Datsenko and Wanner, 2000), as previously described (Pugh et al., 2014).

Plasmid Construction.

All plasmids constructed and used in this study are listed in Table 1. Custom DNA oligonucleotides were synthesized by Integrated DNA Technologies (Coralville, Iowa). Genomic DNA (gDNA) was prepared from cell cultures using the ZR Fungal/Bacterial DNA MiniPrep (Zymo Research, Irvine, Calif.) according to vendor protocols. All genes were PCR amplified with Q5 High-Fidelity DNA Polymerase (New England Biolabs (NEB)) using standard protocols. Amplified linear DNA fragments were purified using the Zymo Research DNA Clean & Concentrator Kit (Zymo Research) according to manufacturer protocols. Once purified, DNA fragments were then digested with appropriate restriction endonuclease enzymes at 37° C. for >6 hours (h). Digested fragments were gel purified using the Zymoclean Gel DNA Recovery Kit (Zymo Research, Irvine, Calif.) and ligated at room temperature for >1 h using T4 DNA ligase (NEB). Ligation reactions were transformed into chemically-competent *E. coli* NEB 10-beta (NEB) and selected by plating on Luria-Bertani (LB) solid agar containing appropriate antibiotics. Transformant pools were subsequently screened by colony PCR and restriction digest mapping. To enable high expression, the backbone of plasmid pY3 (Addgene plasmid #50606; a gift from Prof. Jay Keasling and originally derived from pBbA5a) (Juminaga et al., *Appl. Environ. Microbiol.* 78:89-98 (2012)), was used for expression of PAL2 and FDC1, as well as ARO10. Plasmid pY-PAL2FDC1 was constructed by cloning a previously assembled operon composed of PAL2 from *Arabidopsis thaliana* and FDC1 from *S. cerevisae* from pTpal-fdc (McKenna et al., *Biotechnol. J.* 8:1465-75 (2013)) using the primer pair described by SEQ ID NO:8 and SEQ ID NO:9 and inserting it into the pY3-derived backbone. Plasmid pTrcColaK-styABC was constructed by cloning the native styABC operon from *P. putida* S12 using the primer pair described by SEQ ID NO:10 and SEQ ID NO:11 and inserting it into pTrcColaK.

Assaying SOI Activity in Whole Resting Cells.

SOI activity was assayed in whole resting cells engineered to express styC from *P. putida* S12. More specifically, *E. coli* BW25113 was first transformed with either pTrcColaK-styC or pTrcColaK (as control). Seed cultures were prepared by growing individual colonies from LB-agar plates in 3 mL of LB for ~12 h at 32° C. Seed cultures were used to inoculate 50 mL of LB broth supplemented with 35 mg/L kanamycin in a 250 mL shake flask. Flasks were cultured at 32° C. with shaking for ~8 h, at which time they were induced by addition of isopropyl β-D-1-thiogalactopyranoside (IPTG) at a final concentration of 0.2 mM. Following induction, cultures were incubated at 32° C. overnight, after which cells were then harvested by centrifugation at 3,000×g. The cell pellet was washed twice with pH 7.4 phosphate buffered saline (PBS) solution, and resuspended in 50 mL pH 7.4 PBS solution to a final cell density determined as an optical density at 600 nm ($OD_{600}$) of ~4. For the assay, a series of resting cell suspensions, each with a total volume of 50 mL in a 250 mL shake flask, were prepared at final cell densities of $OD_{600}$~0.01, 0.03, and 0.07 (i.e., by resuspending an appropriate volume of the above stock suspension) in fresh pH 7.4 PBS solution supplemented with (S)-styrene oxide at an initial concentration of 1300 mg/L. Over the course of 6.5 hours, flasks were incubated at 32° C. with shaking at 200 RPM while samples (each 0.5 mL) were periodically taken for HPLC analysis to determine concentrations of residual (S)-styrene oxide and produced 2-phenylacetaldehyde, as described below.

Assaying 2PE Toxicity.

The effects of 2PE on *E. coli* growth rate and yield was determined by monitoring the impacts of its exogenous addition at increasing final concentrations on growing cultures. Approximately 1 ml of an *E. coli* NST74 seed culture was used to inoculate 50 ml of LB broth in a 250 mL shake flask. When cultures reached $OD_{600}$~0.6, 2PE was added to the flasks at an array of final concentrations ranging from 0 to 2 g/L. Culturing then resumed for an additional 6 h with periodic monitoring of $OD_{600}$.

Production of 2PE from Glucose by Engineered *E. coli*.

Seed cultures were grown in 3 mL LB broth supplemented with appropriate antibiotics at 32° C. for 12-16 h. Next, 0.5 mL of seed culture was used to inoculate 50 mL (in 250 mL shake flasks) of pH 6.8 MM1—a phosphate-limited minimal media adapted from McKenna and Nielsen (McKenna and Nielsen, *Metab. Eng.* 13:544-54 (2011)), with the following recipe (in g/L): glucose (20), $MgSO_4.7H_2O$ (0.5), $(NH_4)_2SO_4$ (4.0), MOPS (24.7), $KH_2PO_4$ (0.3), and $K_2HPO_4$ (1.0), as well as 1 mL/L of a trace mineral solution containing (in g/L): Thiamine HCl (0.101), $MnCl_2.4H_2O$ (1.584), $ZnSO_4.7H_2O$ (0.288), $CoCl_2.6H_2O$ (0.714), $CuSO_4$ (0.1596), $H_3BO_3$ (2.48), $(NH_4)_6Mo_7O_{24}.4H_2O$ (0.370), and $FeCl_3$ (0.050). Once inoculated, cultures were grown at 32° C. while shaking at 200 RPM until reaching an $OD_{600}$ of 0.8 (~8 h), at which time they were induced by addition of IPTG at a final concentration of 0.2 mM unless otherwise stated. Following induction, strains were cultured for a total of 72 hours (unless otherwise stated), during which time samples were periodically withdrawn for cell growth and metabolite analysis. Meanwhile, intermittently throughout each culture, pH was increased back to its initial value by adding a minimal volume (typically ~0.2-0.4 mL) of 0.4 g/L $K_2HPO_4$ solution.

Analytical Methods.

Cell growth was measured as $OD_{600}$ using a UV/Vis spectrophotometer (Beckman Coulter DU800, Brea, Calif.). Culture samples were centrifuged at 11,000×g for 4 min to pellet cells, after which 0.25 mL of the resulting supernatant was then transferred to a glass HPLC vial containing an equal volume of 1 N HCl before being sealed with a Teflon-lined cap. Analysis of all aromatic metabolites was performed via high performance liquid chromatography (HPLC; Agilent 1100 series HPLC, Santa Clara, Calif.) using a diode array (UV/Vis) detector. Separation was achieved on a reverse-phase 5 μm Hypersil Gold C18 column (4.6 mm×100 mm; Thermo Fisher, USA) operated at 45° C. using mobile phase consisting of water with 0.1% formic acid (A) and methanol (B), flowing at a constant rate of 0.75 mL/min according to the following gradient: 5% B at 0 min, 5% to 80% B from 0 to 10.67 min, 80% B from 10.67 to 13.33 min, 80% to 5% B from 13.33 to 18.67 min, and 5% B from 18.67 to 20 min. The eluent was monitored using a diode array detector (DAD) set at 215 nm for detection of Phe, trans-cinnamic acid, styrene and (S)-styrene oxide, and 258 nm for detection of 2-phenylacetaldehyde, 2-phenylacetic acid, and 2PE. Glucose and acetate analysis, meanwhile, was performed using the same HPLC system equipped with a refractive index detector (RID) and an Aminex HPX-87H column (BioRad, Hercules, Calif.) operated at 35° C. The column was eluted using 5 mM $H_2SO_4$ as the mobile phase at a constant flow rate of 0.55 mL/min for 20 min. External calibrations were prepared and used to quantify each species of interest.

Results

Comparative Assessment of Alternative 2PE Pathways.

Figure 2:
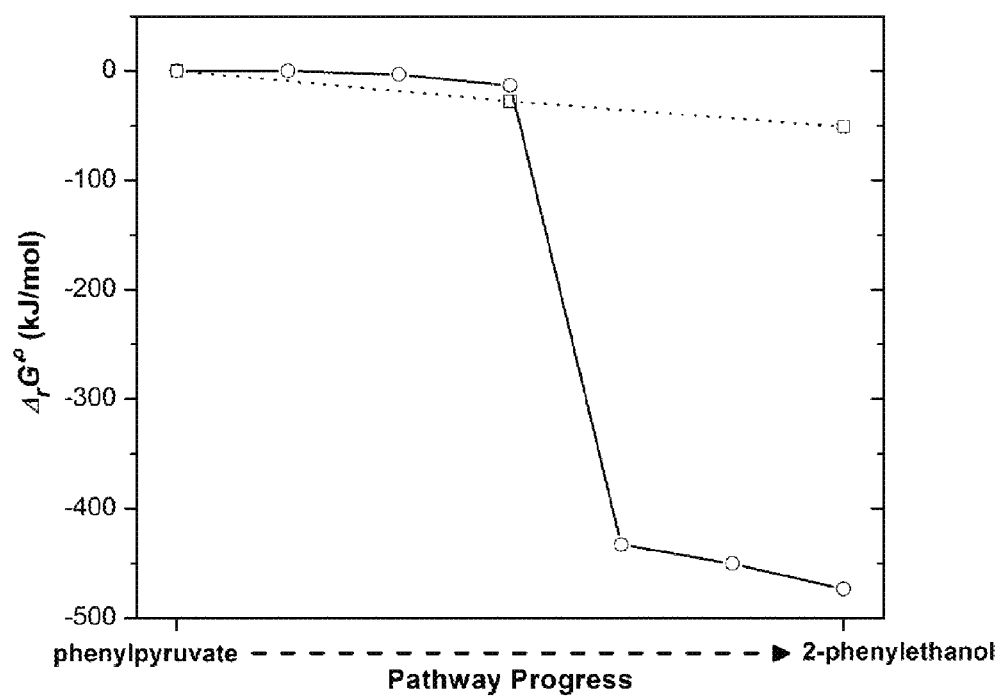
FIG. 2 shows a comparison in the change in Gibbs free energy due to reaction ($\Delta rG'^\circ$) with progress through each of the two pathways (Ehrlich pathway, open squares-dotted line; styrene pathway, open circles-solid line) from phenylpyruvate to 2PE. $\Delta rG'^\circ$ was determined for each reaction using the eQuilibrator online tool at a reference state of 25° C., pH 7, and ionic strength of 0.1 M.

As seen in FIG. 1, both the proposed, styrene-derived, and established, Ehrlich, pathways stem from precursors in the SA pathway, namely Phe and phenylpyruvate, respectively. As such, both pathways share the same theoretical yield, estimated as 0.36 g/g on glucose (with functional PTS, based on estimates derived from Varma et al. (1993)). Moreover, both pathways converge at 2-phenylacetaldehyde before its reduction to 2PE, as has been reported to readily occur in *E. coli* via one or more native, NADPH-dependent alcohol dehydrogenases (ADHs; e.g., yqhD, yahK, yjgB) and/or aldo-keto reductases (AKRs; e.g., dkgA, dkgB, yeaE) (Kunjapur et al., *J. Am. Chem. Soc.* 136:11644-11654 (2014); Rodriguez and Atsumi, *Metab. Eng.* 25:227-37 (2014)). However, between the last common precursor (i.e., phenylpyruvate) and 2PE, the two pathways differ greatly and in several important ways. For instance, unlike the Ehrlich pathway, which employs only one foreign enzyme, the styrene-derived pathway is instead composed of four heterologous steps. However, despite its length, the thermodynamic driving force associated with the styrene-derived pathway is nearly 10-fold greater than that of the Ehrlich pathway. More specifically, when compared from phenylpyruvate to 2PE, the net change in Gibbs free energy of reaction ($\Delta_r G'^\circ$) for the Ehrlich pathway is −50.9 kJ/mol compared to −474.4 kJ/mol for the styrene-derived pathway (FIG. 2); the bulk of the difference being due to the highly favorable conversion of styrene to (S)-styrene oxide via styrene monooxygenase (NADH-dependent, encoded by styAB), which contributes −419.4 kJ/mol (or 88%) to the total $\Delta_r G'^\circ$ of the pathway (Flamholz et al., 2012). As a consequence, however, the styrene-derived pathway consumes twice as many reducing equivalents (1 NADH and 1 NADPH per molecule of 2PE produced) than the Ehrlich pathway (only 1 NADPH). Accordingly, whereas similarities certainly exist, both 2PE pathways appear to possess their own unique and inherent merits and limitations, the likes of which were next experimentally investigated.

Engineering 2PE Pathways.

Figure 3:
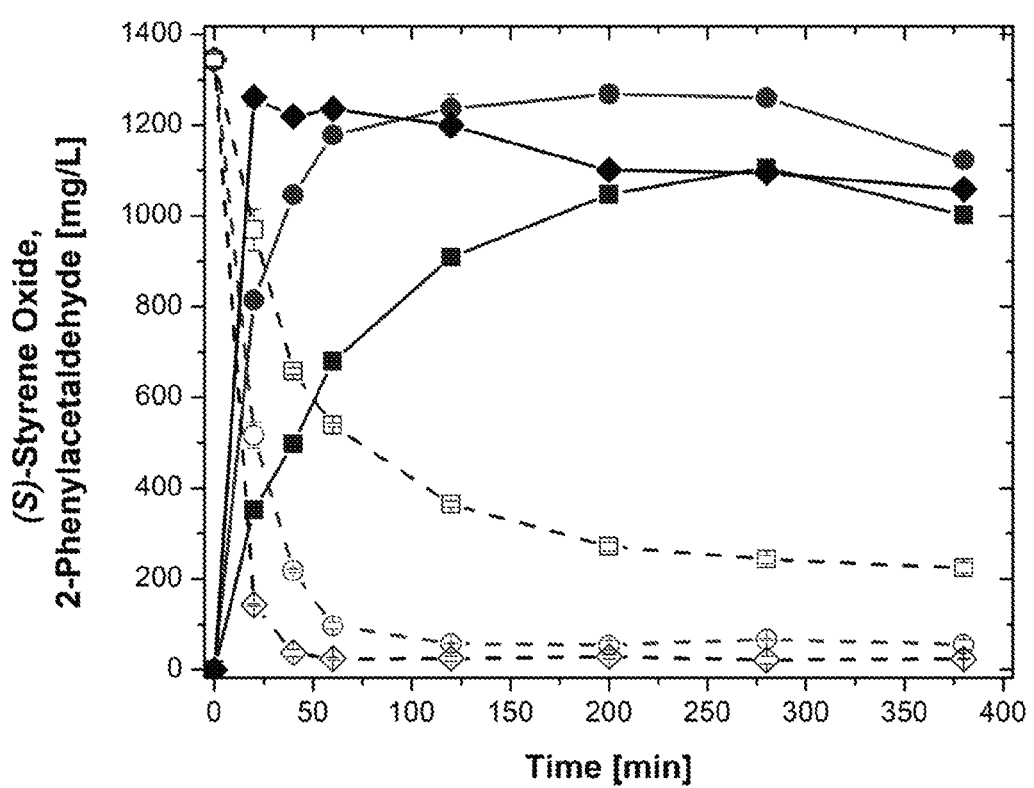
FIG. 3 shows screening styrene oxide isomerase enzyme activity using *E. coli* BW25113 pColaK-styC whole resting cells. Conversion of (S)-styrene oxide (open shapes, dotted line) to 2-phenylacetaldehyde (solid shapes, solid line) by StyC using three different cell densities ($OD_{600}$~0.01, 0.03, and 0.07 are squares, circles, and diamonds, respectively). Error bars reported at one standard deviation from triplicate experiments.

Construction of the styrene-derived 2PE pathway began from our previously-engineered (S)-styrene oxide pathway, comprised of PAL2 from *A. thaliana*, FDC1 from *S. cerevisiae*, and styAB from *P. putida* S12 (McKenna and Nielsen, 2011; McKenna et al., 2013). To then convert (S)-styrene oxide to 2-phenylacetaldehyde (before its reduction to 2PE by native ADHs/AKRs), however, it was first necessary to identify a suitable gene encoding SOI activity. Of particular interest was styC from *P. putida* S12 (Panke et al., *Appl. Environ. Microbiol.* 64:2032-43 (1998)), which together with styAB, functions as part of its native styrene degradation pathway (O'Connor et al., *Appl. Environ. Microbiol.* 61:544-8 (1995); Warhurst and Fewson, *J. Appl. Bacteriol.* 77:597-606 (1994)). Following the cloning and subsequent expression of styC in *E. coli* BW25113 pTrc-ColaK-styC, a whole resting cell assay was performed wherein, as seen in FIG. 3, recombinant SOI activity was demonstrated via the conversion of exogenous (S)-styrene oxide to 2-phenylacetaldehyde (note: control experiments using *E. coli* BW25113 pTrcColaK showed no conversion of (S)-styrene oxide; data not shown). Initially, the assay was performed at a high cell density (i.e., $OD_{600}$~4; representing that of a typical culture), however, under such conditions 100% conversion was achieved in <10 min with stoichiometric yield (data not shown). To slow the net reaction rate and allow for improved monitoring, the experiment was repeated at lower cell densities (specifically, $OD_{600}$ of 0.01, 0.03, and 0.07). In this case, increasing cell density resulted in faster rates of (S)-styrene oxide consumption and 2-phenylacetaldehyde production, with the former reaching as high as 5.6 g/L-h. For comparison, when previously assayed under analogous conditions, styAB-expressing *E. coli* resting cells produced (S)-styrene oxide from exogenous styrene at rates reaching only as high as ~0.1 g/L-h; albeit at much higher cell densities ($OD_{600}$~1).

Based on this result, styC was cloned for expression as part of the full, styrene-derived pathway, in this case as part of the natural styABC operon (encoding both SMO and SOI) and expressed via a $P_{trc}$ promoter as plasmid pTrcColaK-styABC. To complete the pathway, PAL2 and FDC1 were cloned in a synthetic operon for expression via $P_{lacUV5}$ on plasmid pY-PAL2FDC1. In the case of the Ehrlich pathway, meanwhile, PPDC plays a key role as the first committed pathway step. Previously, Atsumi et al. evaluated 5 different PPDC isozymes (namely those encoded by ARO10, PDC6 and THI3 from *S. cervisiae*, kivd from *L. lactis*, and pdc from *C. acetobutylicum*) in *E. coli*, ultimately finding ARO10 to support the greatest 2PE production from glucose (Atsumi et al., 2008). Accordingly, ARO10 was fused to a $P_{lacUV5}$ promoter for its expression from pY-ARO10.

Demonstrating and Comparing 2PE Production Via Alternative Pathways.

The Ehrlich and styrene-derived pathways were both constructed as described in Table 1 and first introduced and expressed in *E. coli* NST74 (a previously-engineered, Phe-overproducing strain (Tribe, U.S. Pat. No. 4,681,852)), with the resulting strains producing 158±12 and 182±4 mg/L of 2PE, respectively. However, in addition to 2PE, both strains also co-produced 2-phenylacetic acid as a major byproduct, whose final titers reached 352±12 and 503±21 mg/L, respectively. In *E. coli*, 2-phenylacetaldehyde is converted to 2-phenylacetic acid via its native, $NAD^+$-dependent 2-phenylacetaldehyde dehydrogenase, encoded by feaB (FIG. 1) (Parrott et al., 1987). In this case, the ~1.5-fold greater 2-phenylacetic acid production accompanying the styrene-derived pathway was likely due to its aforementioned increased redox requirement, which would be partially balanced via oxidation of 2-phenylacetaldehyde to 2-phenylacetic acid (regenerating 1 NADH; FIG. 1). To eliminate undesirable accumulation of 2-phenylacetic acid, feaB was next deleted from NST74. When introduced and expressed in NST74 ΔfeaB, 2-phenylacetic acid production was no longer detected for either the Ehrlich or styrene-derived pathway and, after 72 hours, 2PE titers now reached 552±14 and 643±29 mg/L, respectively; in both cases at similar glucose yields (35.1±0.5 and 37.7±1.2 mg/g, or 9.7 and 10.5% of the theoretical maximum).

Figure 4:
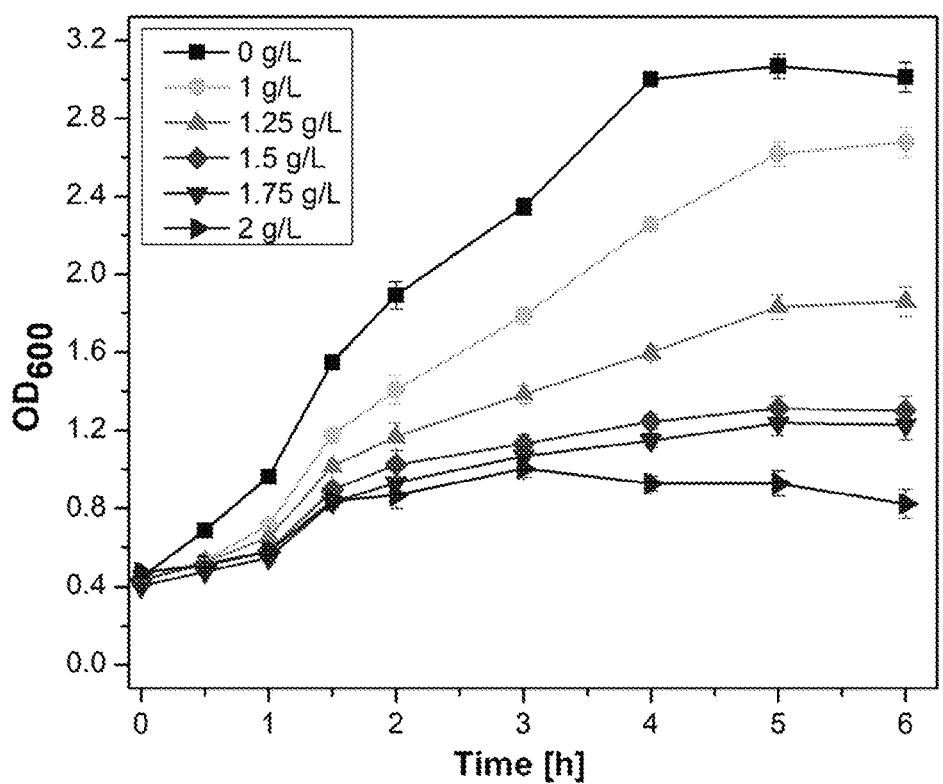
FIG. 4 shows the growth response of *E. coli* NST74 following exogenous 2PE addition at final concentrations of 0 g/L (control; square), 1 g/L (circle), 1.25 g/L (upright triangle), 1.5 g/L (diamond), 1.75 g/L (inverted triangle) and 2 g/L (right triangle). Error bars reported at one standard deviation from triplicate experiments.

To assess if 2PE production in these initial strains was perhaps limited by end-product inhibition, a growth challenge study was performed determine to the response of *E. coli* growth to the addition of exogenous 2PE at a range of increasing final concentrations (FIG. 4). While growth rate and yield were reduced in the presence of as little as 1 g/L 2PE, severe growth inhibition did not occur until reaching about 2 g/L 2PE. This compares well with prior reports wherein 2PE was reported to inhibit *E. coli* at levels of ~1 g/L (Kang et al., 2014), and suggests that, at least in these initial strains, 2PE production by either pathway was likely not yet limited by end-product inhibition.

Host Strain Engineering to Increase Precursor Availability.

Figure 5:
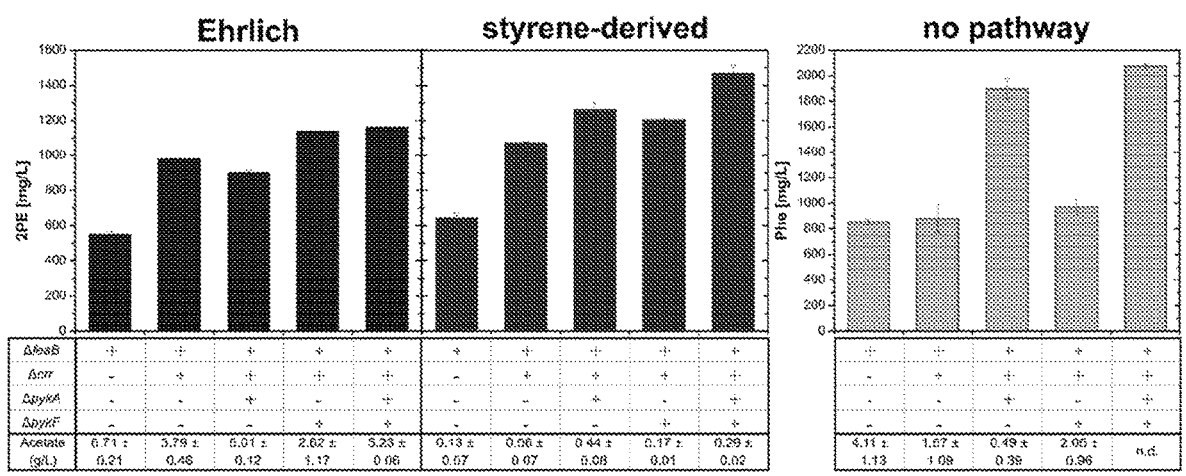
FIG. 5 shows the final titers of 2PE after 72 hours (h) of culturing for the Ehrlich (left) and styrene-derived (center) pathways in *E. coli* NST74 strains harboring various deletions of genes feaB, crr, pykA and pykF. Also shown for comparison are final Phe titers by the same host strain in the absence of either pathway (right). Final acetate concentrations are also shown (n.d. indicates not detected). Error bars reported at one standard deviation from duplicate experiments.

Robust 2PE production by either pathway depends on ample production of SA pathway precursors (FIG. 1), which in turn is known to benefit from increased availability of phosphoenolpyruvate (PEP). Noda et al. previously reported deletion of pykF and pykA (encoding pyruvate kinase isozymes I and II, respectively, which convert PEP to pyruvate, producing ATP) as an effective strategy for promoting PEP availability, in their case also enhancing the production of various chorismate-derived aromatic products (Noda et al., 2016). Meanwhile, it has been further demonstrated that PEP availability can be improved via the partial inactivation (i.e., by deleting crr, encoding $IIA^{Glc}$) of the glucose-specific phosphotransferase system (PTS; which facilitates glucose uptake via its phosphorylation at the expense of PEP) (Gosset, 2005). Said mutation also further benefits the culture by reducing rates of glucose uptake which, in turn, also decreases overflow metabolism and the associated production of unwanted (and potentially inhibitory) acetate (Gosset, 2005; Liu et al., 2014). Accordingly, NST74 ΔfeaB was further engineered to systematically introduce ΔpykA, ΔpykF, and Δcrr mutations, upon which the resulting strains were tested for their relative ability to support 2PE production via the two pathways. The resulting 2PE titers are compared in FIG. 5, along with the relative effects of the same mutations on Phe production by each host strain (i.e., in the absence of either pathway) for comparison. As can be seen, compared to the above results using NST74 ΔfeaB as host, deletion of crr had a significant effect on 2PE production by both the Ehrlich and styrene-derived pathways, improving final titers by 77% and 67%, respectively. Deletion of crr also resulted in reductions in acetate accumulation, in each case by 45-60%. Meanwhile, the additional, combined deletion of both pykA and pykF led to even further improvements in 2PE production by both the Ehrlich and styrene-derived pathways, reaching 1163±3 and 1468±47 mg/L (or 9.52±0.02 and 12.02±0.38 mM), respectively, after 72 hours (increases of 19% and 37% relative to using NST74 ΔfeaB Δcrr as host). Interestingly, as is most prominent in the case of the styrene-derived pathway, individual deletion of just pykA or pykF alone gave little or no improvement, suggesting that full inactivation of pyruvate kinase activity is necessary to realize the beneficial effects of this strategy. That said, analogous experiments in the absence of the pathway (i.e., for Phe production) suggest the ΔpykA mutation to perhaps be most important (FIG. 5). For comparison, in the absence of either pathway, NST74 ΔfeaB Δcrr ΔpykA ΔpykF produced a total of 2076±19 mg/L (12.57±0.11 mM) Phe. Accordingly, and assuming constant flux through the SA pathway in each case, this suggests that the styrene-derived pathway was more efficient than the Ehrlich pathway (96 vs. 76%) at assimilating and ultimately converting their corresponding endogenous precursor to 2PE.

Interestingly, acetate production via the styrene-derived pathway was minimal (i.e., 0.5-0.44 g/L) regardless of which host background was used and, in all cases, was 14- to 71-fold lower than when expressing the Ehrlich pathway. Most strikingly, although in the absence of either pathway acetate accumulation was undetected with NST74 ΔfeaB Δcrr ΔpykA ΔpykF, upon introduction of the Ehrlich pathway, acetate levels rose back up to 5.23±0.06 g/L. As said behavior was unique to the Ehrlich pathway, we hypothesized that acetate production could perhaps be occurring as a result of ARO10 promiscuity. Decarboxylation of pyruvate, for example, yields acetaldehyde which, in turn, could be oxidized to acetate via *E. coli*'s $NADP^+$-dependent aldehyde dehydrogenase (encoded by aldB) (Ho and Weiner, 2005). To provide an initial assessment of this proposed phenomena, control cultures were prepared of *E. coli* BW25113 pY-ARO10 which were then grown in the absence or presence of 6 g/L exogenously-supplied sodium pyruvate. After 48 hours, as seen in Table 2, accumulated acetate levels were 3.8-fold higher following sodium pyruvate addition (5.41 vs. 1.41 g/L). While more detailed characterizations are needed, these findings certainly support the proposed, ARO10-associated mechanism of acetate accumulation.

Culture Condition Manipulation to Further Improve 2PE Production.

Figure 6:
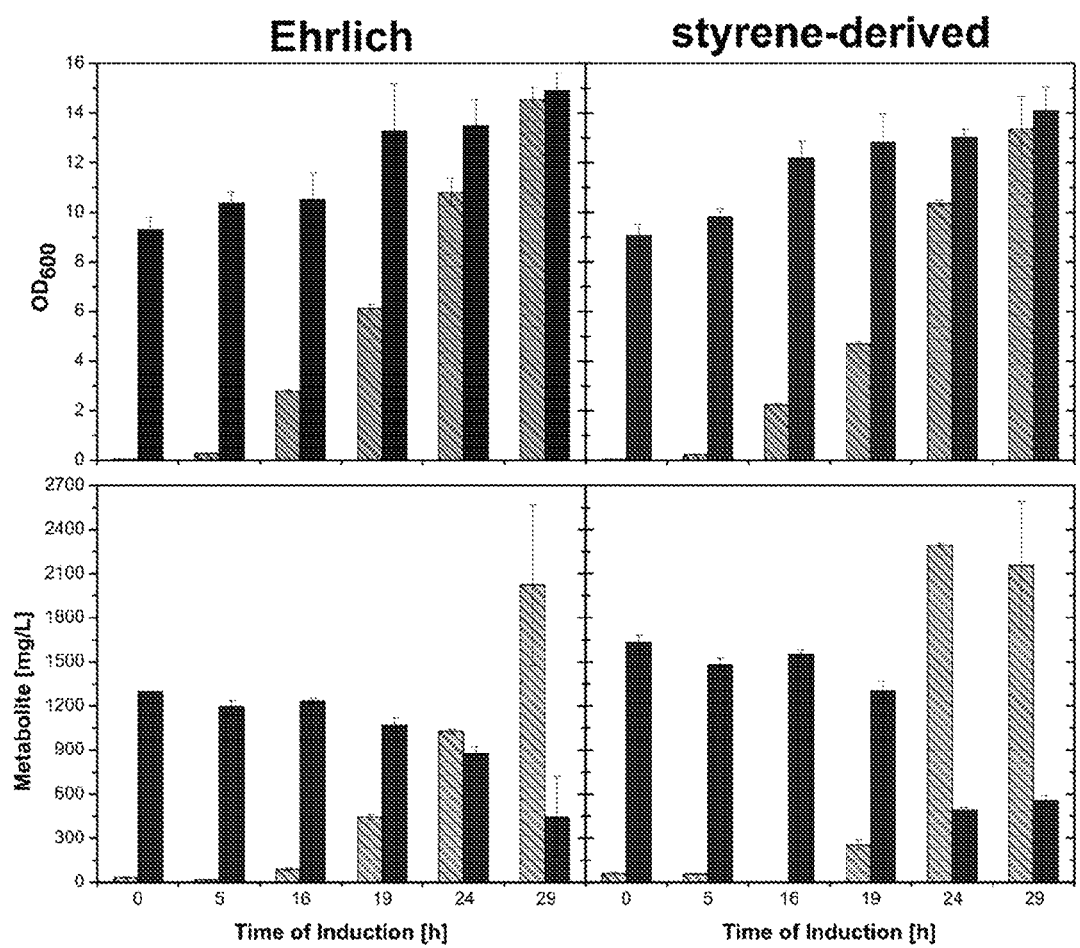
FIG. 6 shows the effect of induction timing on production of 2PE and Phe as well as growth after 72 hours by both pathways when expressed in *E. coli* NST74 ΔfeaB Δcrr ΔpykA ΔpykF. Upper panels: final $OD_{600}$ (dark, solid) and $OD_{600}$ at time of induction for the Ehrlich (left; light, striped) and styrene-derived (right; light, striped) pathways. Lower panels: Final concentrations of 2PE (dark, solid) and Phe (striped, gold) for the Ehrlich (left) and styrene-derived (right) pathways. Error bars reported at one standard deviation from duplicate experiments.
Figure 7:
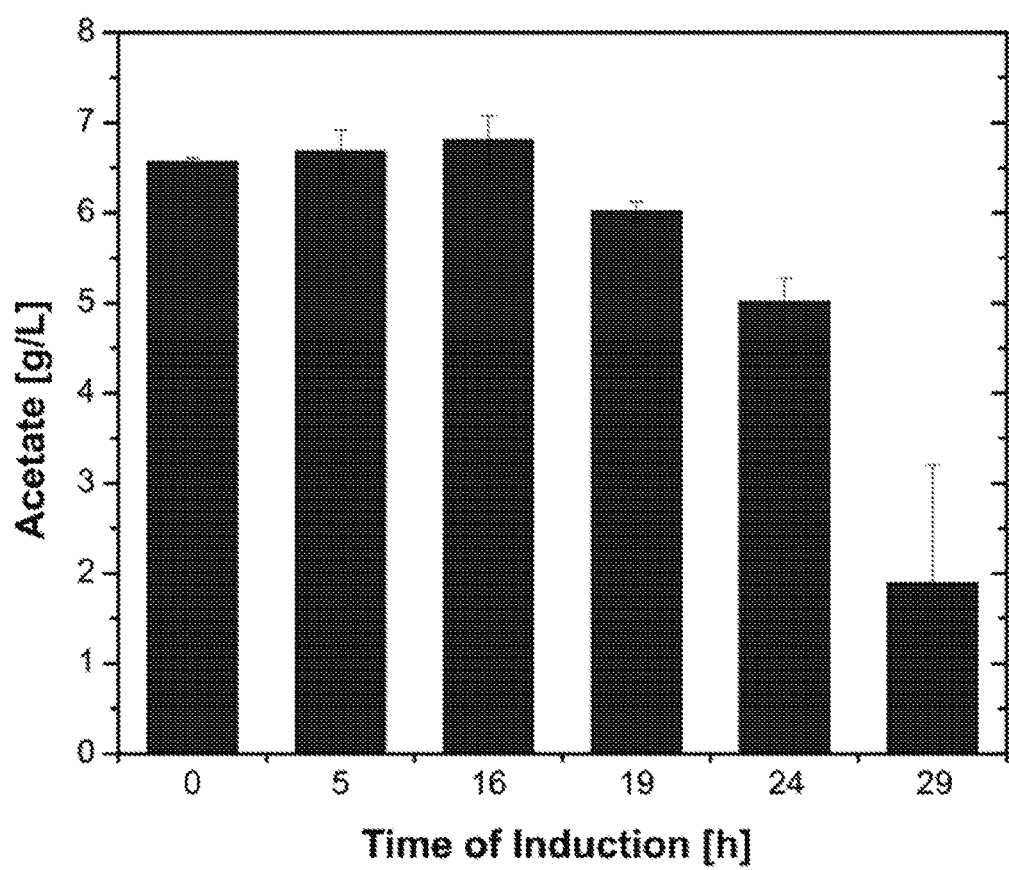
FIG. 7 shows acetate accumulation after 72 h by *E. coli* NST74 ΔfeaB Δcrr ΔpykA ΔpykF expressing the Ehrlich pathway, as a function of induction timing. Error bars reported at one standard deviation from duplicate experiments.

Induction timing and initial substrate concentration were next manipulated to further improve 2PE production. In the first case, the timing of IPTG-induced expression of the Ehrlich and styrene-derived pathways in NST74 ΔfeaB Δcrr ΔpykA ΔpykF was investigated at six different points (from inoculation to late exponential phase), the results of which are compared in FIG. 6. In both cases, induction at inoculation gave the greatest final 2PE titers, suggesting greater net flux through each pathway was realized when each was given maximal time to compete for endogenous precursors (consistent with observations of reduced biomass production at earlier inductions; FIG. 6). In contrast, when induced too late (i.e., at 19 hours or beyond), neither pathway effectively competed for its requisite precursor, which instead was then assimilated into additional biomass and/or accumulated Phe. In the case of the Ehrlich pathway, net acetate accumulation followed a similar pattern to that of 2PE production, with less build-up occurring for later inductions (FIG. 6 and FIG. 7; reductions in 2PE and acetate production were 66% and 71%, respectively, when cultures were induced at inoculation versus after 29 hours); an observation that further supports the above hypothesis that significant acetate byproduct formation is ARO10-associated, perhaps resulting due to its promiscuity.

Figure 8:
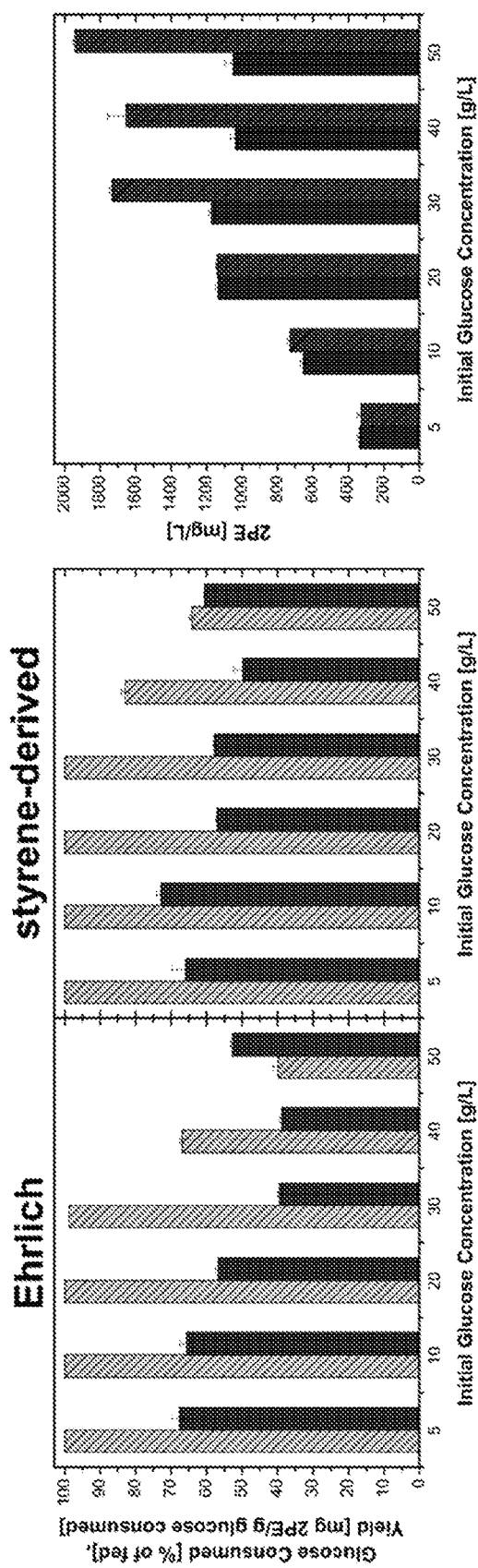
FIG. 8 shows the effect of various initial concentrations of glucose (ranging from 5 to 50 g/L) for 2PE production of *E. coli* NST74 ΔfeaB Δcrr ΔpykA ΔpykF induced at inoculation. Left: Glucose consumed as a percentage of glucose fed (light, striped) and mass yield of 2PE from glucose (dark, solid) after 96 h of culturing for the Ehrlich (left) and styrene-derived (center) pathways. Right: 2PE titers for the Ehrlich (dark, solid) and styrene-derived (light, striped) pathways at the 96 h mark are shown for various concentrations of initial glucose. Error bars reported at one standard deviation from duplicate experiments.

All of the above 2PE production studies were performed by initially supplying each culture with 20 g/L glucose which, in all cases, was fully consumed within 72 hours (data not shown). As this suggests a possible substrate limitation, a series of batch experiments were next performed wherein increasing amounts of initial glucose (5 to 50 g/L) were instead supplied, in all cases using the best-performing host strain (i.e., NST74 ΔfeaB Δcrr ΔpykA ΔpykF) and optimal induction timing (i.e., at inoculation). FIG. 8 compares glucose consumption, along with 2PE yield and final titers for both pathways. In all cases, glucose is fully consumed when initially supplied at 5 to 30 g/L, with higher initial glucose levels resulting in increased 2PE titers. At higher initial glucose concentrations (i.e., 40 and 50 g/L), however, clear differences emerge with respect to the two pathways. Though also declining (perhaps due to a nutrient limitation or onset of substrate inhibition), greater conversion at higher glucose loadings and, as a result, increased 2PE titers and yields remain possible via the styrene-derived pathway. Ultimately, when supplied with 50 g/L glucose, 2PE titers via the styrene-derived pathway reached their maximum level of 1941±13 mg/L at a yield of 60.5±0.3 mg/g (16.8% of theoretical); a final 2PE titer ~2-fold greater than the highest value reported to date for *E. coli* expressing the Ehrlich pathway.

Figure 9:
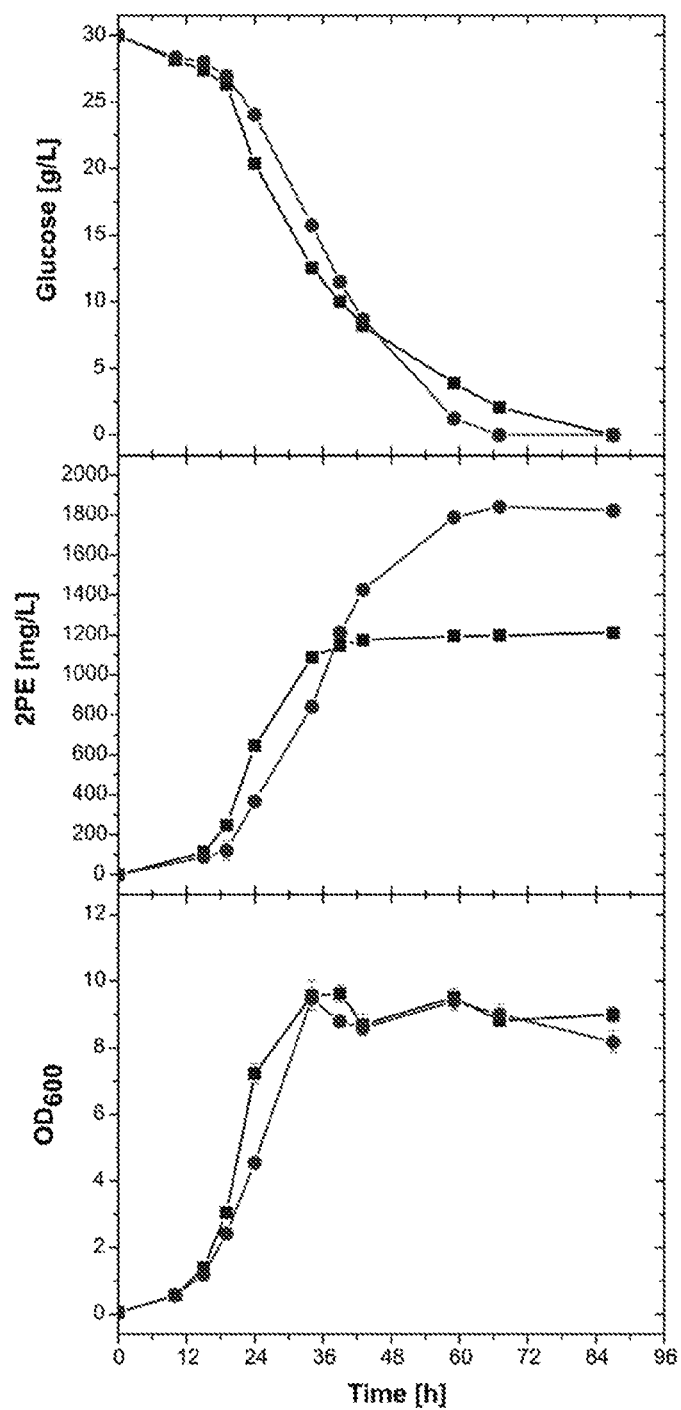
FIG. 9 shows the time course analysis of 2PE production metrics over 87 h in the Ehrlich (squares) and styrene-derived (circles) pathways with 30 g/L initial glucose in *E. coli* NST74 ΔfeaB Δcrr ΔpykA ΔpykF induced at inoculation. Upper: glucose consumption. Middle: 2PE production. Lower: $OD_{600}$. Error bars reported at one standard deviation from duplicate experiments.

A series of batch cultures were lastly performed to investigate the dynamics of 2PE production via both pathways, in each case utilizing NST74 ΔfeaB Δcrr ΔpykA ΔpykF as host while supplying 30 g/L glucose (to ensure full utilization) and performing induction at inoculation. FIG. 9 compares glucose consumption, 2PE production, and biomass accumulation in each case. Initially, rates of all three are slower for the styrene-derived pathway. Notably, for instance, while expressing the Ehrlich pathway, average volumetric rates of glucose consumption and 2PE production during the first 24 h were 401±13 and 26.8±0.2 mg/L-h, respectively, compared to just 248±7 and 15.3±0.1 mg/L-h for the styrene-derived pathway. However, by ~36 h, 2PE production by the Ehrlich pathway (which occurred coincidently with cell growth) levels off, whereas production continues for an additional ~30 h via the styrene-derived pathway (during which time cell growth had already entered the stationary phase). Ultimately, after 87 hours, final 2PE titers reached 1823±16 and 1212±17 mg/L for the styrene-derived and Ehrlich pathways, respectively, at yields of 60.8±0.5 and 40.4±0.6 mg/g—both improvements of ~50%. Finally, it should be noted that, by 36 hours, acetate accumulation in cultures expressing the Ehrlich pathway had surpassed 1.4 g/L while remaining under 0.5 g/L for the styrene-derived pathway (data not shown), suggesting that the ability of the styrene-derived pathway to mitigate inhibitory byproduct accumulation might contribute to its capacity to maintain longer periods of productivity and greater net 2PE production.

Discussion and Conclusion

A novel route to 2PE has been engineered as a robust alternative to the established, Ehrlich pathway. Ultimately, for example, when compared under otherwise analogous conditions (FIG. 9), 2PE titers and yields were about 50% greater via the styrene-derived versus Ehrlich pathway, with final titers capable of approaching ~2 g/L with additional glucose supplementation. As characterized via both in silico analyses and experimental studies, relative to the Ehrlich pathway, the styrene-derived 2PE pathway was found to possess its own unique and notable advantages, as well as certain caveats. For example, as has been previously characterized with respect to (S)-styrene oxide production (also produced via styrene, as in FIG. 1) (McKenna et al., 2013), the highly favorable SMO reaction (which is largely responsible for the ~10-fold greater thermodynamic driving force of the styrene-derived pathway), serves to effectively 'pull' more precursor (i.e., Phe) into the pathway. This phenomenon is further supported in the case of 2PE production, noting that conversion of the endogenous precursors via the styrene-derived pathway was 96% versus just 76% by the Ehrlich pathway. Additionally, and in contrast to the Ehrlich pathway, which branches off from native metabolism (i.e., at phenylpyruvate), the styrene-derived pathway instead extends from a terminal pathway metabolite (i.e., Phe; FIG. 1). In this way, the styrene-derived pathway also importantly avoids introducing a competitive 'branch point'. In the Ehrlich pathway, for example, as PPDC (e.g., ARO10, $K_m$=100 µM (Kneen et al., 2011)) must directly compete against native Phe aminotransferase (i.e., TyrB, $K_m$=12 µM (Gelfand and Steinberg, 1977)) for available phenylpyruvate, kinetic limitations can in turn reduce the flux of metabolites that enter the pathway at its first committed step. Of course, deletion of tyrB eliminates such competition, preserving phenylpyruvate for the Ehrlich pathway, however, said mutation comes at the cost of a Phe auxotrophy, thereby necessitating its supplementation and leading to increased media costs and reduced scalability. Viewed in this way, the styrene-derived pathway more broadly provides improved compatibility with the host background.

One of the most significant differences between employing the two 2PE pathways concerns not the product, but rather a byproduct, namely acetate. Previously, as further demonstrated here, improvements in the production of Phe and/or other aromatic derivatives can be realized by inactivation of crr, pykA, and pykF. Whereas deletion of crr reduces rates of glucose consumption and thus acetate production (Liu et al., 2014), Noda et al. reported a 4.5-fold decrease in acetate yield by deleting both pykA and pykF (Noda et al., 2016). However, as evidenced by the results of FIG. 5, even when using a host background virtually deficient in acetate accumulation (i.e., NST74 ΔfeaB Δcrr ΔpykA ΔpykF), acetate production reemerged upon introduction of the Ehrlich pathway, reaching final concentrations as high as 5.23±0.06 g/L. Previous studies have found that acetate concentrations above 1 g/L can deter biomass and protein production, reduce protein stability, and lower pH, causing cell lysis (De Mey et al., 2007). Accordingly, and regardless of the specific mechanism, the ability to avoid acetate byproduct accumulation when employing the styrene-derived pathway is postulated as a significant reason for the ability of this pathway to support superior 2PE production metrics. Though still warranting further investigation, acetate byproduct accumulation when expressing the Ehrlich pathway is thought to be a result of ARO10 promiscuity. Although prior reports suggest that, at least with respect to its native expression in *S. cerevisiae*, ARO10 displays minimal activity on pyruvate (with in vitro assays reporting $k_{cat}/k_m$=200 and 0.035 mM$^{-1}$·s$^{-1}$ for phenylpyruvate and pyruvate, respectively (Kneen et al., 2011)), here, the experimental evidence presented suggests otherwise, that is at least with respect to its recombinant in vivo function in *E. coli*. That said, whereas such effects might be avoided by constructing the Ehrlich pathway using a PPDC with greater recombinant specificity, to the best of our knowledge, such an isozyme has so far not been identified/reported. Thus, for now at least, an additional advantage of the styrene-derived pathway appears to the greater substrate specificity of its associated enzymes. And, as high acetate accumulation can be a substantial hurdle in scale-up, especially with high glucose levels (Xu et al., 1999), such prospects might be improved by the alternative application of this novel pathway.

With final 2PE titers via the styrene-derived pathway ultimately approaching ~2 g/L (at high glucose loading), and in contrast to preliminary cultures, said output now approaches the toxicity limit of 2PE. As the mode of aromatic toxicity against bacteria has most commonly been reported to be associated with their accumulation within and disruption of the cytoplasmic membrane (Sikkema et al., 1994), a similar phenomenon was also anticipated here. In fact, with a toxicity threshold determined as ~2 g/L, the present observations of 2PE toxicity agree well with previously-reported model used to predict the toxicity of various aromatic bioproducts (e.g., styrene, (S)-styrene oxide, and various phenolics) based on estimates of the membrane-water partitioning coefficient ($K_{M/W}$) (McKenna et al., 2013). Meanwhile, various strategies for in situ 2PE removal have also been investigated, including, for example, via its extraction in a biphasic ionic liquid system which gave 3- to 5-fold increases in 2PE production by *S. cerevisiae* (Sendovski et al., 2010). Other approaches, meanwhile, including pervaporation (Etschmann et al., 2005) and solid-phase extraction (i.e., using hydrophobic resins) (Achmon et al., 2011) have shown as high as 10-fold improvements in 2PE productivity, and would likely provide similar benefits to the strains developed here.

TABLE 1

Strains, plasmids, and pathways constructed and/or used in this Example.

| Strains | Description | Source |
|---|---|---|
| *E. coli* NST74 | aroH367, tyrR366, tna-2, lacY5, aroF394(fbr), malT384, pheA101(fbr), pheO352, aroG397(fbr) | ATCC 31884 |
| *E. coli* BW25113 | Δ(araD-araB)567, ΔlacZ4787::rrnB-3, λ⁻, rph-1, Δ(rhaD-rhaB)568, hsdR514 | CGSC |
| *E. coli* NEB-10 beta | araD139 Δ(ara,leu)7697 fhuA lacX74 galK16 galE15 mcrA f80d(lacZΔM15)recA1 relA1 endA1 nupG rpsL rph spoT1Δ(mrr-hsdRMS-mcrBC) | NEB |
| *S. cerevisiae* W303 | Source of ARO10, FDC1 | ATCC 200060 |
| *P. putida* S12 | Source of styABC | ATCC 700801 |
| *E. coli* NST74 ΔfeaB | ΔfeaB mutation in *E. coli* NST74 | This Example |
| *E. coli* NST74 ΔfeaB Δcrr | Δcrr mutation in *E. coli* NST74 ΔfeaB | This Example |
| *E. coli* NST74 ΔfeaB Δcrr ΔpykA | ΔpykA mutation in *E. coli* NST74 ΔfeaB Δcrr | This Example |

TABLE 1-continued

Strains, plasmids, and pathways constructed and/or used in this Example.

| | | |
|---|---|---|
| *E. coli* NST74 ΔfeaB Δcrr ΔpykF | ΔpykF mutation in *E. coli* NST74 ΔfeaB Δcrr | This Example |
| *E. coli* NST74 ΔfeaB Δcrr ΔpykA ΔpykF | ΔpykF mutation in *E. coli* NST74 ΔfeaB Δcrr ΔpykA | This Example |

| Plasmids | Features and/or Construction | Source |
|---|---|---|
| pTrcColaK | ColA ori, lacI$^q$, Kan$^r$, P$_{Trc}$ | McKenna et al. (2013) |
| pBbA5a (via pY3) | p15A ori, lacI, Amp$^r$, P$_{lacUV5}$ | Juminaga et al. (2012) |
| pCP20 | FLP, ts-rep, [cI857](lambda)(ts), Amp$^r$ | CGSC |
| pKD46 | repA101(ts) and R101 ori, Amp$^r$, araC, araBp | CGSC |
| pTpal-fdc | PAL2 from *A. thaliana* and FDC1 of *S. cerevisiae* inserted into the NcoI and XbaI and SbfI and HindIII sites of pTrc99A | McKenna et al. (2013) |
| pY-PAL2FDC1 | PAL2-FDC1 operon from pTpal-fdc inserted into the BglII and XhoI sites of pY3 | This Example |
| pTrcColaK-styC | styC of *P. putida* S12 inserted into the PstI and HindIII sites of pTrcColaK | This Example |
| pTrcColaK-styABC | styABC of *P. putida* S12 inserted into the XbaI and HindIII sites of pTrcColaK | This Example |
| pY-ARO10 | ARO10 of *S. cerevisiae* inserted into the BglII and XhoI sites of pY3 | This Example |

| Pathways | Description: Composed of plasmids | Source |
|---|---|---|
| Ehr | 'Ehrlich' pathway: pY-ARO10 | This Example |
| Sty | 'Styrene-derived' pathway: pY-PAL2FDC1 and pTrcColaK-styABC | This Example |

TABLE 2

Acetate accumulation in cultures of *E. coli* BW25113 pY-aro10 grown in pH 6.8 MM1 media supplemented with sodium pyruvate at a total concentration of 0 or 6 g/L (note: sodium pyruvate was added periodically through the cultures, at each of 8, 18 and 27 h in each case being added at a final concentration of 2 g/L).

| Hours after inoculation [h] | 0 g/L sodium pyruvate fed | 6 g/L sodium pyruvate fed |
|---|---|---|
| | Acetate [g/L] | |
| 18 | 0.09 | 0.54 |
| 27 | 0.49 | 0.95 |
| 48 | 1.41 | 5.41 |

Example 2

The embodiments described here demonstrate the production of 2-phenylethanol (2PE) in engineered microorganisms via the heterologous metabolic pathways described herein.

Materials and Methods

All genes were PCR amplified using a BioRad iCycler system, Phusion DNA Polymerase (New England Biolabs, Ipswich, Mass., USA), and custom oligonucleotide primers. PCR cycling and reaction conditions were standardized according to manufacturer instructions. All PCR amplified DNA fragments were purified using the Zyppy DNA Clean and Concentrator kit (Zymo Research, Irvine, Calif., USA). Gene fragments and plasmids were treated by endonuclease digestion according to manufacturer's protocols. All digested fragments were first gel purified using the Zyppy DNA purification kit (Zymo Research, Irvine, Calif., USA) and then ligated with T4 DNA Ligase (New England Biolabs, Ipswich, Mass., USA) at 4° C. overnight before the mixture was then transformed into chemically competent *E. coli* NEB10-Beta. Transformants were selected on LB solid agar with appropriate antibiotics and cultured at 37° C. overnight. Transformant pools were screened using colony PCR with final confirmation by gene sequencing. PAL2 was amplified from cDNA of clone U12256 from the *Arabidopsis* Biological Resource Center (ABRC, Columbus, Ohio, USA) using primers given by SEQ ID NO: 12 and SEQ ID NO: 13 and cloned into pTrc99a, resulting in construction of the plasmid pTpal. FDC1 was amplified from gDNA of *Saccharomyces cerevisiae* using primers given by SEQ ID NO: 15 and SEQ ID NO: 15 and cloned into pTpal, resulting in construction of the plasmid pTpal-fdc.

Seed cultures were grown in 3 mL LB broth supplemented with appropriate antibiotics at 32° C. for 12-16 h. Next, 0.5 mL of seed culture was used to inoculate 50 mL (in 250 mL shake flasks) of pH 6.8 MM1—a phosphate-limited minimal media adapted from McKenna and Nielsen, with the following recipe (in g/L): glucose (20), MgSO$_4$·7H$_2$O (0.5), (NH$_4$)$_2$SO$_4$ (4.0), MOPS (24.7), KH$_2$PO$_4$ (0.3), and K$_2$HPO$_4$ (1.0), as well as 1 mL/L of a trace mineral solution containing (in g/L): MnCl$_2$·4H$_2$O (1.584), ZnSO$_4$·7H$_2$O (0.288), CoCl$_2$.6H$_2$O (0.714), CuSO$_4$ (0.1596), H$_3$BO$_3$ (2.48), (NH$_4$)$_6$Mo$_7$O$_{24}$.4H$_2$O (0.370), and FeCl$_3$ (0.050). Once inoculated, cultures were grown at 32° C. while shaking at 200 RPM until reaching an OD$_{600}$ of 0.8 (~8 h), at which time they were induced by addition of IPTG at a final concentration of 0.2 mM. Following induction, strains were cultured for a total of 72 h (unless otherwise stated), during which time samples were periodically withdrawn for cell growth and metabolite analysis. Meanwhile, intermittently throughout each culture, pH was increased back to its initial value by adding a minimal volume (typically ~0.2-0.4 mL) of 0.4 g/L K$_2$HPO$_4$ solution.

Results

As a proof of concept, pTpal-fdc was co-transformed with pTrcColaK-styABC into *E. coli* NST74 with a feaB deletion (NST74ΔfeaB). After culturing for 96 h, the cultures grew to an OD$_{600}$ of 11.0±1.0 with 2PE titers final reaching 759.8±3.0 mg/L with no accumulation of intermediates (including L-phenylalanine). Additionally, the same two plasmids were also co-transformed into NST74ΔfeaB with various additional deletions shown to improve production of L-phenylalanine (i.e., deletion of crr, pykA, pykF).

Table 3 (below) demonstrates production of 2PE after 72 hours of culturing in MM1 media by *E. coli* NST74ΔfeaB with engineered with additional deletions to the genes crr, pykA, and/or pykF. Each strain was co-transformed with pTpal-fdc and pTrcColaK-styABC. In this case, it can be seen that NST74ΔfeaB was the host strain that supported the highest 2PE production using these plasmids.

TABLE 3

2PE Production

| Host Strain | 2PE Titer (mg/L) |
| --- | --- |
| NST74ΔfeaBΔcrr | 507 ± 159 |
| NST74ΔfeaBΔpykA | 688 ± 354 |
| NST74ΔfeaBΔcrrΔpykA | 605 ± 28 |
| NST74ΔfeaBΔcrrΔpykF | 704 ± 348 |
| NST74ΔfeaBΔcrrΔpykAΔpykF | 531 ± 158 |

SEQUENCE LISTING

SEQ ID NO:1 is the nucleotide sequence of a gene from *A. thaliana* encoding an phenylalanine ammonia-lyase (PAL2).
SEQ ID NO:2 is the nucleotide sequence of a gene from *S. cerevisiae* encoding a ferulate decarboxylase (FDC1).
SEQ ID NO:3 is the nucleotide sequence of a gene from *P. putida* S12 encoding subunit A of a styrene monooxygenase (styA).
SEQ ID NO:4 is the nucleotide sequence of a gene from *P. putida* S12 encoding subunit B of a styrene monooxygenase (styB).
SEQ ID NO:5 is the nucleotide sequence of a native gene cluster from *P. putida* S12 encoding both A and B subunits of a styrene oxide isomerase (styAB).
SEQ ID NO:6 is the nucleotide sequence of a gene from *P. putida* S12 encoding a styrene oxide isomerase (styC).
SEQ ID NO:7 is the nucleotide sequence of a native operon from *P. putida* S12 encoding both A and B subunits of a styrene oxide isomerase as well as a styrene oxide isomerase (styABC).
SEQ ID NO:8 is a primer used to amplify PAL2 and FDC1 from pTpal-fdc (McKenna, R., Pugh, S., Thompson, B. and Nielsen, D. R. (2013), Microbial production of the aromatic building-blocks (S)-styrene oxide and (R)-1,2-phenylethanediol from renewable resources. Biotechnology Journal, 8: 1465-1475. doi:10.1002/biot.201300035).
SEQ ID NO:9 is a primer used to amplify PAL2 and FDC1 from pTpal-fdc (McKenna, R., Pugh, S., Thompson, B. and Nielsen, D. R. (2013), Microbial production of the aromatic building-blocks (S)-styrene oxide and (R)-1,2-phenylethanediol from renewable resources. Biotechnology Journal, 8: 1465-1475. doi:10.1002/biot.201300035).
SEQ ID NO:10 is a primer used to amplify styABC from *P. putida* S12.
SEQ ID NO:11 is a primer used to amplify styABC from *P. putida* S12.
SEQ ID NO:12 is a primer used to amplify PAL2 from *A. thaliana* cDNA from clone U12256.
SEQ ID NO:13 is a primer used to amplify PAL2 from *A. thaliana* cDNA from clone U12256.
SEQ ID NO:14 is a primer used to amplify FDC1 from *S. cerevisiae*.
SEQ ID NO:15 is a primer used to amplify FDC1 from *S. cerevisiae*.

SEQ ID NO: 1
LENGTH: 2154
TYPE: DNA
ORGANISM: Arabidopsis thaliana
SEQUENCE: 1
ATGGATCAAATCGAAGCAATGTTGTGCGGCGGAGGAGAGAAGACAAAAGT

GGCGGTTACTACGAAGACTTTGGCAGATCCATTGAATTGGGGTTTAGCAG

CGGATCAAATGAAAGGAAGTCATTTAGATGAAGTGAAGAAGATGGTCGAA

GAGTATCGTAGACCAGTCGTGAATCTTGGCGGAGAAACACTGACGATCGG

ACAAGTTGCTGCCATCTCCACCGTAGGAGGCAGCGTTAAGGTTGAGTTAG

CGGAGACTTCAAGAGCCGGTGTGAAAGCTAGCAGTGATTGGGTTATGGAG

AGCATGAACAAAGGTACTGACAGTTACGGAGTCACCACCGGCTTTGGTGC

TACTTCTCACCGGAGAACCAAAAACGGCACCGCATTACAAACAGAACTCA

TTAGATTTTTGAACGCCGGAATATTCGGAAACACGAAGGAGACATGTCAC

ACACTGCCGCAATCCGCCACAAGAGCCGCCATGCTCGTCAGAGTCAACAC

TCTTCTCCAAGGATACTCCGGGATCCGATTCGAGATCCTCGAAGCGATTA

CAAGTCTCCTCAACCACAACATCTCTCCGTCACTACCTCTCCGTGGAACC

ATTACCGCCTCCGGCGATCTCGTTCCTCTCTCTTACATCGCCGGACTTCT

CACCGGCCGTCCTAATTCCAAAGCCACCGGTCCCGACGGTGAATCGCTAA

CCGCGAAAGAAGCTTTTGAGAAAGCCGGAATCAGTACTGGATTCTTCGAT

TTACAACCTAAGGAAGGTTTAGCTCTCGTTAATGGCACGGCGGTTGGATC

TGGAATGGCGTCGATGGTTCTATTCGAAGCGAATGTCCAAGCGGTGTTAG

CGGAGGTTTTATCAGCGATCTTCGCGGAGGTTATGAGCGGGAAACCTGAG

TTTACCGATCATCTGACTCATCGTTTAAAACATCATCCCGGACAAATCGA

AGCGGCGGCGATAATGGAGCACATACTCGACGGAAGCTCATACATGAAAT

TAGCTCAAAAGGTTCACGAGATGGATCCATTGCAGAAACCAAAACAAGAT

CGTTACGCTCTTCGTACATCTCCTCAATGGCTAGGTCCTCAAATTGAAGT

AATCCGTCAAGCTACGAAATCGATAGAGCGTGAAATCAACTCCGTTAACG

ATAATCCGTTGATCGATGTTTCGAGGAACAAGGCGATTCACGGTGGTAAC

TTCCAAGGAACACCAATCGGAGTTTCTATGGATAACACGAGATTGGCGAT

-continued
TGCTGCGATTGGGAAGCTAATGTTTGCTCAATTCTCTGAGCTTGTTAATG
ATTTCTACAACAATGGACTTCCTTCGAATCTAACTGCTTCGAGTAATCCA
AGTTTGGATTATGGATTCAAAGGAGCAGAGATTGCTATGGCTTCTTATTG
TTCTGAGCTTCAATACTTGGCTAATCCAGTCACAAGCCATGTTCAATCAG
CTGAGCAACATAATCAAGATGTGAACTCTCTTGGTTTGATCTCGTCTCGT
AAAACATCTGAAGCTGTGGATATTCTTAAGCTAATGTCAACAACGTTCCT
TGTGGGATATGTCAAGCTGTTGATTTGAGACATTTGGAGGAGAATCTGA
GACAAACTGTGAAGAACACAGTTTCTCAAGTTGCTAAGAAAGTGTTAACC
ACTGGAATCAACGGTGAGTTACATCCGTCAAGGTTTTGCGAGAAGGACTT
GCTTAAGGTTGTTGATCGTGAGCAAGTGTTCACGTATGTGGATGATCCTT
GTAGCGCTACGTACCCGTTGATGCAGAGACTAAGACAAGTTATTGTTGAT
CACGCTTTGTCCAACGGTGAGACTGAGAAGAATGCAGTGACTTCGATCTT
TCAAAAGATTGGAGCTTTTGAAGAGGAGCTTAAGGCTGTGCTTCCAAAGG
AAGTTGAAGCGGCTAGAGCGGCTTATGGGAATGGAACTGCGCCGATTCCT
AACCGGATTAAGGAATGTAGGTCGTATCCGTTGTATAGGTTCGTGAGGGA
AGAGCTTGGAACGAAGTTGTTGACTGGAGAAAAGGTTGTGTCTCCGGGAG
AGGAGTTTGATAAGGTCTTCACTGCTATGTGTGAAGGTAAACTTATTGAT
CCGTTGATGGATTGTCTCAAGGAATGGAACGGAGCTCCGATTCCGATTTG
CTAA SEQ ID NO: 2
LENGTH: 1512
TYPE: DNA
ORGANISM: Saccharomyces cerevisiae
SEQUENCE: 2
ATGAGGAAGCTAAATCCAGCTTTAGAATTTAGAGACTTTATCCAGGTCTT
AAAAGATGAAGATGACTTAATCGAAATTACCGAAGAGATTGATCCAAATC
TCGAAGTAGGTGCAATTATGAGGAAGGCCTATGAATCCCACTTACCAGCC
CCGTTATTTAAAAATCTCAAAGGTGCTTCGAAGGATCTTTTCAGCATTTT
AGGTTGCCCAGCCGGTTTGAGAAGTAAGGAGAAAGGAGATCATGGTAGAA
TTGCCCATCATCTGGGGCTCGACCCAAAAACAACTATCAAGGAAATCATA
GATTATTTGCTGGAGTGTAAGGAGAAGGAACCTCTCCCCCCAATCACTGT
TCCTGTGTCATCTGCACCTTGTAAAACACATATACTTTCTGAAGAAAAAA
TACATCTACAAAGCCTGCCAACACCATATCTACATGTTTCAGACGGTGGC
AAGTACTTACAAACGTACGGAATGTGGATTCTTCAAACTCCAGATAAAAA
ATGGACTAATTGGTCAATTGCTAGAGGTATGGTTGTAGATGACAAGCATA
TCACTGGTCTGGTAATTAAACCACAACATATTAGACAAATTGCTGACTCT
TGGGCAGCAATTGGAAAAGCAAATGAAATTCCTTTCGCGTTATGTTTTGG
CGTTCCCCCAGCAGCTATTTTAGTTAGTTCCATGCCAATTCCTGAAGGTG
TTTCTGAATCGGATTATGTTGGCGCAATCTTGGGTGAGTCGGTTCCAGTA
GTAAAATGTGAGACCAACGATTTAATGGTTCCTGCAACGAGTGAGATGGT
ATTTGAGGGTACTTTGTCCTTAACAGATACACATCTGGAAGGCCCATTTG
GTGAGATGCATGGATATGTTTTCAAAAGCCAAGGTCATCCTTGTCCATTG
TACACTGTCAAGGCTATGAGTTACAGAGACAATGCTATTCTACCTGTTTC GAACCCCGGTCTTTGTACGGATGAGACACATACCTTGATTGGTTCACTAG
TGGCTACTGAGGCCAAGGAGCTGGCTATTGAATCGGCTTGCCAATTCTG
GATGCCTTTATGCCTTATGAGGCTCAGGCTCTTTGGCTTATCTTAAAGGT
GGATTTGAAAGGGCTGCAAGCATTGAAGACAACGCCTGAAGAATTTTGTA
AGAAGGTAGGTGATATTTACTTTAGGACAAAAGTTGGTTTTATAGTCCAT
GAAATAATTTTGGTGGCAGATGATATCGACATATTTAACTTCAAAGAAGT
CATCTGGGCCTACGTTACAAGACATACACCTGTTGCAGATCAGATGGCTT
TTGATGATGTCACTTCTTTTCCTTTGGCTCCCTTTGTTTCGCAGTCATCC
AGAAGTAAGACTATGAAAGGTGGAAAGTGCGTTACTAATTGCATATTTAG
ACAGCAATATGAGCGCAGTTTTGACTACATAACTTGTAATTTTGAAAAGG
GATATCCAAAAGGATTAGTTGACAAAGTAAATGAAAATTGGAAAAGGTAC
GGATATAAATAA SEQ ID NO: 3
LENGTH: 1248
TYPE: DNA
ORGANISM: Pseudomonas putida S12
SEQUENCE: 3
ATGAAAAAGCGTATCGGTATTGTTGGTGCAGGCACTGCCGGCCTCCATCT
TGGTCTCTTCCTTCGTCAGCATGACGTCGACGTCACTGTGTACACTGATC
GTAAGCCCGATGAGTACAGCGGACTGCGTCTCCTGAATACCGTTGCTCAC
AACGCGGTGACGGTGCAGCGGGAGGTTGCCCTCGACGTCAATGAGTGGCC
GTCTGAGGAGTTTGGTTATTTCGGCCACTACTACTACGTAGGTGGGCCGC
AGCCCATGCGTTTCTACGGTGATCTCAAGGCTCCCAGCCGTGCAGTGGAC
TACCGTCTCTACCAGCCGATGCTGATGCGTGCACTGGAAGCCAGGGGCGG
CAAGTTCTGCTACGACGCGGTGTCTGCCGAAGATCTGGAAGGGCTGTCGG
AGCAGTACGATCTGCTGGTTGTGTGCACTGGTAAATACGCCCTCGGCAAG
GTGTTCGAGAAGCAGTCCGAAAACTCGCCCTTCGAGAAGCCGCAACGGGC
ACTGTGCGTTGGTCTCTTCAAGGGCATCAAGGAAGCACCGATTCGCGCGG
TGACTATGTCCTTCTCGCCAGGGCATGGCGAGCTGATTGAGATTCCAACC
CTGTCGTTCAATGGCATGAGCACAGCGCTGGTGCTCGAAAACCATATTGG
TAGCGATCTGGAAGTTCTCGCCCACACCAAGTATGACGATGACCCGCGTG
CGTTCCTCGATCTGATGCTGGAGAAGCTGGGTAAGCATCATCCTTCCGTT
GCCGAGCGCATCGATCCGCTGAGTTCGACCTTGCCAACAGTTCTCTGGA
CATCCTCCAGGGTGGTGTTGTGCCGGCATTCCGCGACGGTCATGCGACCC
TCAATAACGGCAAAACCATCATTGGGCTGGGCGACATCCAGGCAACTGTC
GATCCGGTCTTGGGCCAGGGCGCGAACATGGCGTCCTATGCGGCATGGAT
TCTGGGCGAGGAAATCCTTGCGCACTCTGTCTACGACCTGCGCTTCAGCG
AACACCTGGAGCGTCGCCGCCAGGATCGCGTGCTGTGTGCCACGCGATGG
ACCAACTTCACTCTGAGCGCTCTCTCGGCACTTCCGCCGGAGTTCCTCGC
CTTCCTTCAGATCCTGAGCCAGAGCCGTGAAATGGCTGATGAGTTCACGG
ACAACTTCAACTACCCGGAACGTCAGTGGGATCGCTTCTCCAGCCCGGAA
CGTATCGGACAGTGGTGCAGTCAGTTCGCACCCACTATCGCGGCCTGA SEQ ID NO: 4
LENGTH: 513
TYPE: DNA
ORGANISM: Pseudomonas putida S12
SEQUENCE: 4
ATGACGTTAAAAAAGATATGGCGGTGGATATCGACTCCACCAACTTCCG
CCAGGCGGTTGCATTGTTCGCGACGGGAATTGCGGTTCTCAGCGCGGAGA
CTGAAGAGGGCGATGTGCACGGCATGACCGTGAACAGTTTCACCTCCATC
AGTCTGGATCCGCCGACTGTGATGGTTTCCCTGAAATCGGGCCGTATGCA
TGAGTTGCTGACTCAAGGCGGACGCTTCGGAGTTAGCCTCTTGGGTGAAA
GCCAGAAGGTGTTCTCGGCATTCTTCAGCAAGCGCGCGATGGATGACACG
CCTCCCCCCGCCTTCACCATTCAGGCCGGCCTTCCCACTCTGCAGGGCGC
CATGGCCTGGTTCGAATGCGAGGTGGAGAGCACGGTTCAAGTACACGACC
ACACGCTCTTCATTGCGCGCGTTAGCGCCTGTGGAACGCCTGAGGCGAAT
ACCCCCCAGCCGCTGCTGTTCTTTGCCAGCCGTTATCACGGCAACCCGTT
GCCACTGAATTGA SEQ ID NO: 5
LENGTH: 1815
TYPE: DNA
ORGANISM: Pseudomonas putida S12
SEQUENCE: 5
ATGAAAAAGCGTATCGGTATTGTTGGTGCAGGCACTGCCGGCCTCCATCT
TGGTCTCTTCCTTCGTCAGCATGACGTCGACGTCACTGTGTACACTGATC
GTAAGCCCGATGAGTACAGCGGACTGCGTCTCCTGAATACCGTTGCTCAC
AACGCGGTGACGGTGCAGCGGGAGGTTGCCCTCGACGTCAATGAGTGGCC
GTCTGAGGAGTTTGGTTATTTCGGCCACTACTACTACGTAGGTGGGCCGC
AGCCCATGCGTTTCTACGGTGATCTCAAGGCTCCCAGCCGTGCAGTGGAC
TACCGTCTCTACCAGCCGATGCTGATGCGTGCACTGGAAGCCAGGGGCGG
CAAGTTCTGCTACGACGCGGTGTCTGCCGAAGATCTGGAAGGGCTGTCGG
AGCAGTACGATCTGCTGGTTGTGTGCACTGGTAAATACGCCCTCGGCAAG
GTGTTCGAGAAGCAGTCCGAAAACTCGCCCTTCGAGAAGCCGCAACGGGC
ACTGTGCGTTGGTCTCTTCAAGGGCATCAAGGAAGCACCGATTCGCGCGG
TGACTATGTCCTTCTCGCCAGGGCATGGCGAGCTGATTGAGATTCCAACC
CTGTCGTTCAATGGCATGAGCACAGCGCTGGTGCTCGAAAACCATATTGG
TAGCGATCTGGAAGTTCTCGCCCACACCAAGTATGACGATGACCCGCGTG
CGTTCCTCGATCTGATGCTGGAGAAGCTGGGTAAGCATCATCCTTCCGTT
GCCGAGCGCATCGATCCGGCTGAGTTCGACCTTGCCAACAGTTCTCTGGA
CATCCTCCAGGGTGGTGTTGTGCCGGCATTCCGCGACGGTCATGCGACCC
TCAATAACGGCAAAACCATCATTGGGCTGGGCGACATCCAGGCAACTGTC
GATCCGGTCTTGGGCCAGGGCGCGAACATGGCGTCCTATGCGGCATGGAT
TCTGGGCGAGGAAATCCTTGCGCACTCTGTCTACGACCTGCGCTTCAGCG
AACACCTGGAGCGTCGCCGCCAGGATCGCGTGCTGTGTGCCACGCGATGG
ACCAACTTCACTCTGAGCGCTCTCTCGGCACTTCCGCCGGAGTTCCTCGC
CTTCCTTCAGATCCTGAGCCAGAGCCGTGAAATGGCTGATGAGTTCACGG
ACAACTTCAACTACCCGGAACGTCAGTGGGATCGCTTCTCCAGCCCGGAA CGTATCGGACAGTGGTGCAGTCAGTTCGCACCCACTATCGCGGCCTGACG
CTATTGCTCCGCTGGTCAAGGCCAGCGGAGCCCTAACTCCTGGGTGATTC
AAATGACGTTAAAAAAGATATGGCGGTGGATATCGACTCCACCAACTTC
CGCCAGGCGGTTGCATTGTTCGCGACGGGAATTGCGGTTCTCAGCGCGGA
GACTGAAGAGGGCGATGTGCACGGCATGACCGTGAACAGTTTCACCTCCA
TCAGTCTGGATCCGCCGACTGTGATGGTTTCCCTGAAATCGGGCCGTATG
CATGAGTTGCTGACTCAAGGCGGACGCTTCGGAGTTAGCCTCTTGGGTGA
AAGCCAGAAGGTGTTCTCGGCATTCTTCAGCAAGCGCGCGATGGATGACA
CGCCTCCCCCCGCCTTCACCATTCAGGCCGGCCTTCCCACTCTGCAGGGC
GCCATGGCCTGGTTCGAATGCGAGGTGGAGAGCACGGTTCAAGTACACGA
CCACACGCTCTTCATTGCGCGCGTTAGCGCCTGTGGAACGCCTGAGGCGA
ATACCCCCCAGCCGCTGCTGTTCTTTGCCAGCCGTTATCACGGCAACCCG
TTGCCACTGAATTGA SEQ ID NO: 6
LENGTH: 510
TYPE: DNA
ORGANISM: Pseudomonas putida S12
SEQUENCE: 6
ATGCTTCATGCCTTCGAACGCAAAATGGCCGGCCACGGCATCCTGATGAT
CTTCTGCACCCTTCTATTTGGTGTTGGTCTTTGGATGAACTTGGTTGGCG
GCTTTGAAATCATCCCGGGATACATCATCGAGTTTCATGTCCCGGGTTCC
CCTGAGGGCTGGGCGAGGGCTCATTCCGGCCCCGCACTGAATGGAATGAT
GGTGATAGCAGTGGCATTCGTTTTGCCCAGCCTTGGCTTCGCCGATAAGA
CGGCGCGCTTGCTGGGCAGCATTATCGTCCTGGACGGTTGGTCGAACGTC
GGTTTCTACCTTTTCTCCAACTTCTCTCCCAATCGTGGCCTGACCTTCGG
CCCCAACCAATTTGGGCCTGGCGATATCTTCAGCTTCCTCGCCCTGGCTC
CCGCCTATCTGTTTGGTGTTCTCGCAATGGGGGCGCTCGCAGTGATCGGC
TACCAGGCATTGAAGAGCACCCGTTCTCGTAAAGCTGTTCCGCACGCTGC
TGCGGAATGA SEQ ID NO: 7
LENGTH: 2394
TYPE: DNA
ORGANISM: Pseudomonas putida S12
SEQUENCE: 7
ATGAAAAAGCGTATCGGTATTGTTGGTGCAGGCACTGCCGGCCTCCATCT
TGGTCTCTTCCTTCGTCAGCATGACGTCGACGTCACTGTGTACACTGATC
GTAAGCCCGATGAGTACAGCGGACTGCGTCTCCTGAATACCGTTGCTCAC
AACGCGGTGACGGTGCAGCGGGAGGTTGCCCTCGACGTCAATGAGTGGCC
GTCTGAGGAGTTTGGTTATTTCGGCCACTACTACTACGTAGGTGGGCCGC
AGCCCATGCGTTTCTACGGTGATCTCAAGGCTCCCAGCCGTGCAGTGGAC
TACCGTCTCTACCAGCCGATGCTGATGCGTGCACTGGAAGCCAGGGGCGG
CAAGTTCTGCTACGACGCGGTGTCTGCCGAAGATCTGGAAGGGCTGTCGG
AGCAGTACGATCTGCTGGTTGTGTGCACTGGTAAATACGCCCTCGGCAAG
GTGTTCGAGAAGCAGTCCGAAAACTCGCCCTTCGAGAAGCCGCAACGGGC
ACTGTGCGTTGGTCTCTTCAAGGGCATCAAGGAAGCACCGATTCGCGCGG
TGACTATGTCCTTCTCGCCAGGGCATGGCGAGCTGATTGAGATTCCAACC

CTGTCGTTCAATGGCATGAGCACAGCGCTGGTGCTCGAAAACCATATTGG

TAGCGATCTGGAAGTTCTCGCCCACACCAAGTATGACGATGACCCGCGTG

CGTTCCTCGATCTGATGCTGGAGAAGCTGGGTAAGCATCATCCTTCCGTT

GCCGAGCGCATCGATCCGGCTGAGTTCGACCTTGCCAACAGTTCTCTGGA

CATCCTCCAGGGTGGTGTTGTGCCGGCATTCCGCGACGGTCATGCGACCC

TCAATAACGGCAAAACCATCATTGGGCTGGGCGACATCCAGGCAACTGTC

GATCCGGTCTTGGGCCAGGGCGCGAACATGGCGTCCTATGCGGCATGGAT

TCTGGGCGAGGAAATCCTTGCGCACTCTGTCTACGACCTGCGCTTCAGCG

AACACCTGGAGCGTCGCCGCCAGGATCGCGTGCTGTGTGCCACGCGATGG

ACCAACTTCACTCTGAGCGCTCTCTCGGCACTTCCGCCGGAGTTCCTCGC

CTTCCTTCAGATCCTGAGCCAGAGCCGTGAAATGGCTGATGAGTTCACGG

ACAACTTCAACTACCCGGAACGTCAGTGGGATCGCTTCTCCAGCCCGGAA

CGTATCGGACAGTGGTGCAGTCAGTTCGCACCCACTATCGCGGCCTGACG

CTATTGCTCCGCTGGTCAAGGCCAGCGGAGCCCTAACTCCTGGGTGATTC

AAATGACGTTAAAAAAAGATATGGCGGTGGATATCGACTCCACCAACTTC

CGCCAGGCGGTTGCATTGTTCGCGACGGGAATTGCGGTTCTCAGCGCGGA

GACTGAAGAGGGCGATGTGCACGGCATGACCGTGAACAGTTTCACCTCCA

TCAGTCTGGATCCGCCGACTGTGATGGTTTCCCTGAAATCGGGCCGTATG

CATGAGTTGCTGACTCAAGGCGGACGCTTCGGAGTTAGCCTCTTGGGTGA

AAGCCAGAAGGTGTTCTCGGCATTCTTCAGCAAGCGCGCGATGGATGACA

CGCCTCCCCCCGCCTTCACCATTCAGGCCGGCCTTCCCACTCTGCAGGGC

GCCATGGCCTGGTTCGAATGCGAGGTGGAGAGCACGGTTCAAGTACACGA

CCACACGCTCTTCATTGCGCGCGTTAGCGCCTGTGGAACGCCTGAGGCGA

ATACCCCCCAGCCGCTGCTGTTCTTTGCCAGCCGTTATCACGGCAACCCG

TTGCCACTGAATTGATTGCGCACGAACAAAACAACAAAAACCGGTGAGGC

CTTTCTGTGCCGATCACCGGAAGAGGAGATAGCCATGCTTCATGCCTTCG

AACGCAAAATGGCCGGCCACGGCATCCTGATGATCTTCTGCACCCTTCTA

TTTGGTGTTGGTCTTTGGATGAACTTGGTTGGCGGCTTTGAAATCATCCC

GGGATACATCATCGAGTTTCATGTCCCGGGTTCCCCTGAGGGCTGGGCGA

GGGCTCATTCCGGCCCCGCACTGAATGGAATGATGGTGATAGCAGTGGCA

TTCGTTTTGCCCAGCCTTGGCTTCGCCGATAAGACGGCGCGCTTGCTGGG

CAGCATTATCGTCCTGGACGGTTGGTCGAACGTCGGTTTCTACCTTTTCT

CCAACTTCTCTCCCAATCGTGGCCTGACCTTCGGCCCCAACCAATTTGGG

CCTGGCGATATCTTCAGCTTCCTCGCCCTGGCTCCCGCCTATCTGTTTGG

TGTTCTCGCAATGGGGGCGCTCGCAGTGATCGGCTACCAGGCATTGAAGA

GCACCCGTTCTCGTAAAGCTGTTCCGCACGCTGCTGCGGAATGA

SEQ ID NO: 8
LENGTH: 38
TYPE: DNA
ORGANISM: artificial sequence
FEATURE:
OTHER INFORMATION: Primer

SEQUENCE: 8
GGAAGATCTAGGAGGTAACCAATGGATCAAATCGAAGC

SEQ ID NO: 9
LENGTH: 33
TYPE: DNA
ORGANISM: artificial sequence
FEATURE:
OTHER INFORMATION: Primer

SEQUENCE: 9
TTCCTCGAGCTTCTCTCATCCGCCAAAACAGCC

SEQ ID NO: 10
LENGTH: 41
TYPE: DNA
ORGANISM: artificial sequence
FEATURE:
OTHER INFORMATION: Primer

SEQUENCE: 10
ATATCTAGACTAGGAGGCAGAACATGAAAAAGCGTATCGGT

SEQ ID NO: 11
LENGTH: 27
TYPE: DNA
ORGANISM: artificial sequence
FEATURE:
OTHER INFORMATION: Primer

SEQUENCE: 11
ACTAAGCTTTCATTCCGCAGCAGCGTG

SEQ ID NO: 12
LENGTH: 37
TYPE: DNA
ORGANISM: artificial sequence
FEATURE:
OTHER INFORMATION: Primer

SEQUENCE: 12
TATCCATGGGCGGGAGGTAACCAATGGATCAAATCGA

SEQ ID NO: 13
LENGTH: 27
TYPE: DNA
ORGANISM: artificial sequence
FEATURE:
OTHER INFORMATION: Primer

SEQUENCE: 13
ATTTCTAGATTAGCAAATCGGAATCGG

SEQ ID NO: 14
LENGTH: 43
TYPE: DNA
ORGANISM: artificial sequence
FEATURE:
OTHER INFORMATION: Primer

SEQUENCE: 14
ATACCTGCAGGGGGAGGAATTATATGAGGAAGCTAAATCCAGC

SEQ ID NO: 15
LENGTH: 35
TYPE: DNA
ORGANISM: artificial sequence
FEATURE:
OTHER INFORMATION: Primer

SEQUENCE: 15
ATTAAGCTTTTATTTATATCCGTACCTTTTCCAAT

We claim:

1. A recombinant organism comprising,
   (i) at least one heterologous gene encoding an enzyme having phenylalanine ammonia lyase (PAL) activity,
   (ii) at least one heterologous gene encoding an enzyme having trans-cinnamic acid decarboxylase (CADC) activity,
   (iii) at least one heterologous gene encoding an enzyme having styrene monooxygenase (SMO) activity,
   (iv) at least one heterologous gene encoding an enzyme having styrene oxide isomerase (SOI) activity, and
   (v) at least one gene encoding an enzyme having 2-phenylacetaldehyde reductase (PAR) activity,
   wherein the organism is capable of producing 2-phenylethanol from a fermentable carbon substrate,
   wherein the organism is not capable of producing 2-phenylacetic acid by an enzyme having 2-phenylacetaldehyde dehydrogenase (PADH) activity.

2. The organism of claim 1, wherein the organism is *Escherichia coli*.

3. The organism of claim 2, wherein the organism is a phenylalanine overproducing strain of *E. coli*.

4. The organism of claim 1, wherein the gene encoding a polypeptide having phenylalanine ammonia lyase activity is derived from *Arabidopsis thaliana*.

5. The organism of claim 1, wherein the gene encoding polypeptides having trans-cinnamic acid decarboxylase activity is derived from *Saccharomyces cerevisiae*.

6. The organism of claim 1, wherein the gene encoding a polypeptide having styrene monooxygenase activity is derived from *Pseudomonas putida*.

7. The organism of claim 1, wherein the gene encoding a polypeptide having styrene oxide isomerase activity is derived from *Pseudomonas putida*.

8. A method of producing 2-phenylethanol comprising the steps of,
   (i) contacting the recombinant organism of claim 1 with a fermentable carbon substrate, and
   (ii) growing the recombinant organism for a time sufficient to produce 2-phenylethanol.

9. The method of claim 8, wherein the fermentable carbon substrate is selected from the group consisting of monosaccharides, oligosaccharides, polysaccharides, glycerol, carbon dioxide, methanol, methane, formaldehyde, formate, amino acids, and carbon-containing amines.

10. The method of claim 8, wherein the fermentable carbon substrate is selected from the group consisting of glucose, xylose, and glycerol.

11. The method of claim 8, wherein the fermentable carbon substrate is selected from the group consisting of lignin-derived aromatic monomers, lignin-derived aromatic oligomers and combinations thereof.

12. The method of claim 8, wherein the fermentable carbon substrate is a biomass hydrolysate.

13. The organism of claim 1, wherein an endogenous gene encoding an enzyme having PADH activity is deleted.

14. The organism of claim 1, wherein the organism lacks an endogenous gene encoding an enzyme having PADH activity.

* * * * *